(12) United States Patent
Hamada et al.

(10) Patent No.: US 8,097,211 B2
(45) Date of Patent: Jan. 17, 2012

(54) ANALYZER

(75) Inventors: Yuichi Hamada, Kobe (JP); Masaharu Shibata, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 315 days.

(21) Appl. No.: 12/399,379

(22) Filed: Mar. 6, 2009

(65) Prior Publication Data

US 2009/0325274 A1 Dec. 31, 2009

(30) Foreign Application Priority Data

Jun. 30, 2008 (JP) ................................ 2008-169915
Feb. 16, 2009 (JP) ................................ 2009-32162

(51) Int. Cl.
*G01N 33/00* (2006.01)

(52) U.S. Cl. ........ 422/67; 422/54; 422/68.1; 435/286.2; 435/287.1; 436/48; 436/54

(58) Field of Classification Search .................. None
See application file for complete search history.

(56) References Cited

U.S. PATENT DOCUMENTS

| | | | | |
|---|---|---|---|---|
| 3,193,359 A | * | 7/1965 | Baruch et al. | 422/65 |
| 3,501,273 A | * | 3/1970 | Agner Kjell | 422/65 |
| 4,699,767 A | * | 10/1987 | Aihara | 422/65 |
| 5,658,800 A | * | 8/1997 | Lessard et al. | 436/178 |
| 5,876,670 A | * | 3/1999 | Mitsumaki et al. | 422/65 |
| 5,882,594 A | * | 3/1999 | Kawaguchi et al. | 422/64 |
| 7,264,111 B2 | | 9/2007 | Veiner | |
| 7,283,217 B2 | | 10/2007 | Ikeuchi et al. | |
| 2007/0110617 A1 | * | 5/2007 | Nagai et al. | 422/65 |

FOREIGN PATENT DOCUMENTS

| | | |
|---|---|---|
| JP | 9-43248 A | 2/1997 |
| JP | 11-295321 A | 10/1999 |

* cited by examiner

*Primary Examiner* — In Suk Bullock
*Assistant Examiner* — Timothy G Kingan
(74) *Attorney, Agent, or Firm* — Brinks Hofer Gilson & Lione

(57) ABSTRACT

An analyzer comprising: a first specimen holder configured to hold a plurality of first specimen containers; a conveying assembly for conveying the first specimen containers held in the first specimen holder; a second specimen holder arranged at a position higher than an upper end of the first specimen containers held in the first specimen holder; a holder moving assembly for moving the second specimen holder so as to pass the upper side of at least one of the first specimen containers held in the first specimen holder; a container transferring assembly for transferring at least one of the first specimen containers from the first specimen holder to the second specimen holder; and a controller for controlling the holder moving assembly and the container transferring assembly, is disclosed.

19 Claims, 25 Drawing Sheets ic
ANALYZER

RELATED APPLICATIONS

This application claims priority under 35 U.S.C. §119 to Japanese Patent Application Nos. JP2008-169915 filed Jun. 30, 2008, and JP2009-032162 filed Feb. 16, 2009, the entire contents of which are hereby incorporated by references.

FIELD OF THE INVENTION

The present invention relates to an analyzer capable of measuring a continuous measurement specimen measured successively, and a priority specimen measured in preference to the continuous measurement specimen.

BACKGROUND

An analyzer including a continuous measurement specimen holder configured to be able to hold a plurality of specimen containers accommodating the specimen to be continuously measured, and a priority specimen holder configured to be able to hold a specimen container accommodating the priority specimen measured in preference to the specimen to be continuously measured is known (see e.g., US Patent Publication No. 2007-110617).

US Patent Publication No. 2007-110617 discloses an analyzer including a holding mount setting portion configured to be able to hold a plurality of specimen containers accommodating the specimen to be continuously measured, and a sample container setting portion configured to be able to hold a specimen container accommodating the priority specimen measured in preference to the specimen to be continuously measured. This analyzer is able to respond to measurement of both the continuous measurement specimen to be continuously measured and the priority specimen to be measured in preference to the continuous measurement specimen, and the sample container setting portion moves to a position where the specimen container accommodating the priority specimen is set through the side of the holding mount setting portion when setting the specimen container accommodating the priority specimen in the sample container setting portion.

However, in the analyzer described in US Patent Publication No. 2007-110617, the measurement of both the continuous measurement specimen to be continuously measured and the priority specimen to be measured in preference to the continuous measurement specimen can be responded, and the sample container setting portion is moved to a position where the specimen container accommodating the priority specimen is set through the side of the holding mount setting portion, and thus a space occupied by the holding mount setting portion and a space necessary when the sample container setting portion moves need to be separately arranged in plan view. Thus, there is a problem that the installation area of the analyzer increases.

The analyzer described in US Patent Publication No. 2007-110617 is configured to move the specimen container held by the holding mount setting portion in a vertical direction and a horizontal direction by a container transferring mechanism to be set in the sample container setting portion and to aspirate the specimen set in the sample container setting portion, when measuring the continuous measurement specimen.

However, the analyzer described in US Patent Publication No. 2007-110617 is configured to move the specimen container held by the holding mount setting portion in a vertical direction and a horizontal direction by a container transferring mechanism to be set in the sample container setting portion, and thus the container transferring mechanism needs to move in the horizontal direction on the upper side of the specimen container held by the holding mount setting portion. Therefore, the container transferring mechanism interferes with the sample container setting portion if the installation area of the analyzer is reduced by arranging the sample container setting portion on the upper side of the holding mount setting portion.

SUMMARY OF THE INVENTION

The scope of the present invention is defined solely by the appended claims, and is not affected to any degree by the statements within this summary.

A first aspect of the present invention is an analyzer comprising: a first specimen holder configured to hold a plurality of first specimen containers accommodating a continuous measurement specimen to be continuously measured; a conveying assembly for conveying the first specimen containers held in the first specimen holder; a second specimen holder arranged at a position higher than an upper end of the first specimen containers held in the first specimen holder and configured to hold at least one of the first specimen containers and a second specimen container accommodating a priority measurement specimen to be measured in preference to the continuous measurement specimen; a holder moving assembly for moving the second specimen holder so as to pass the upper side of at least one of the first specimen containers held in the first specimen holder; a container transferring assembly for transferring at least one of the first specimen containers from the first specimen holder to the second specimen holder; and a controller for controlling the holder moving assembly and the container transferring assembly to execute steps of: raising at least one of the first specimen containers held in the first specimen holder to the upper side of the second specimen holder in a state the second specimen holder does not exist on the upper side, moving the second specimen holder to the lower side of the raised first specimen container, and setting the first specimen container in the second specimen holder by lowering the first specimen container.

A second aspect of the present invention is an analyzer comprising: a first specimen holder configured to hold a plurality of first specimen containers accommodating a continuous measurement specimen to be continuously measured; a conveying assembly for conveying the first specimen containers held in the first specimen holder; a second specimen holder arranged at a position higher than an upper end of the first specimen containers held in the first specimen holder and configured to hold a second specimen container accommodating a priority measurement specimen to be measured in preference to the continuous measurement specimen; and a holder moving assembly for moving the second specimen holder so as to pass the upper side of at least one of the first specimen containers held in the first specimen holder.

A third aspect of the present invention is an analyzer comprising: a first specimen holder configured to hold a plurality of first specimen containers accommodating a continuous measurement specimen to be continuously measured; a second specimen holder arranged at a position higher than an upper end of the first specimen containers held in the first specimen holder and configured to hold at least one of the first specimen containers and a second specimen container accommodating a priority measurement specimen to be measured in preference to the continuous measurement specimen; a holder moving assembly for moving the second specimen holder so as to pass the upper side of at least one of the first specimen containers held in the first specimen holder; a container transferring assembly for transferring at least one of the first specimen containers from the first specimen holder to the second specimen holder; and an aspiration section for aspirating the specimen from the first and the second specimen containers set in the second specimen holder; wherein the holder moving assembly is configured to move the second specimen holder to a position where the specimen is aspirated by the aspiration section.

DETAILED DESCRIPTION OF THE PREFERRED EMBODIMENTS

The preferred embodiments of the present invention will be described hereinafter with reference to the drawings.

Figure 1:
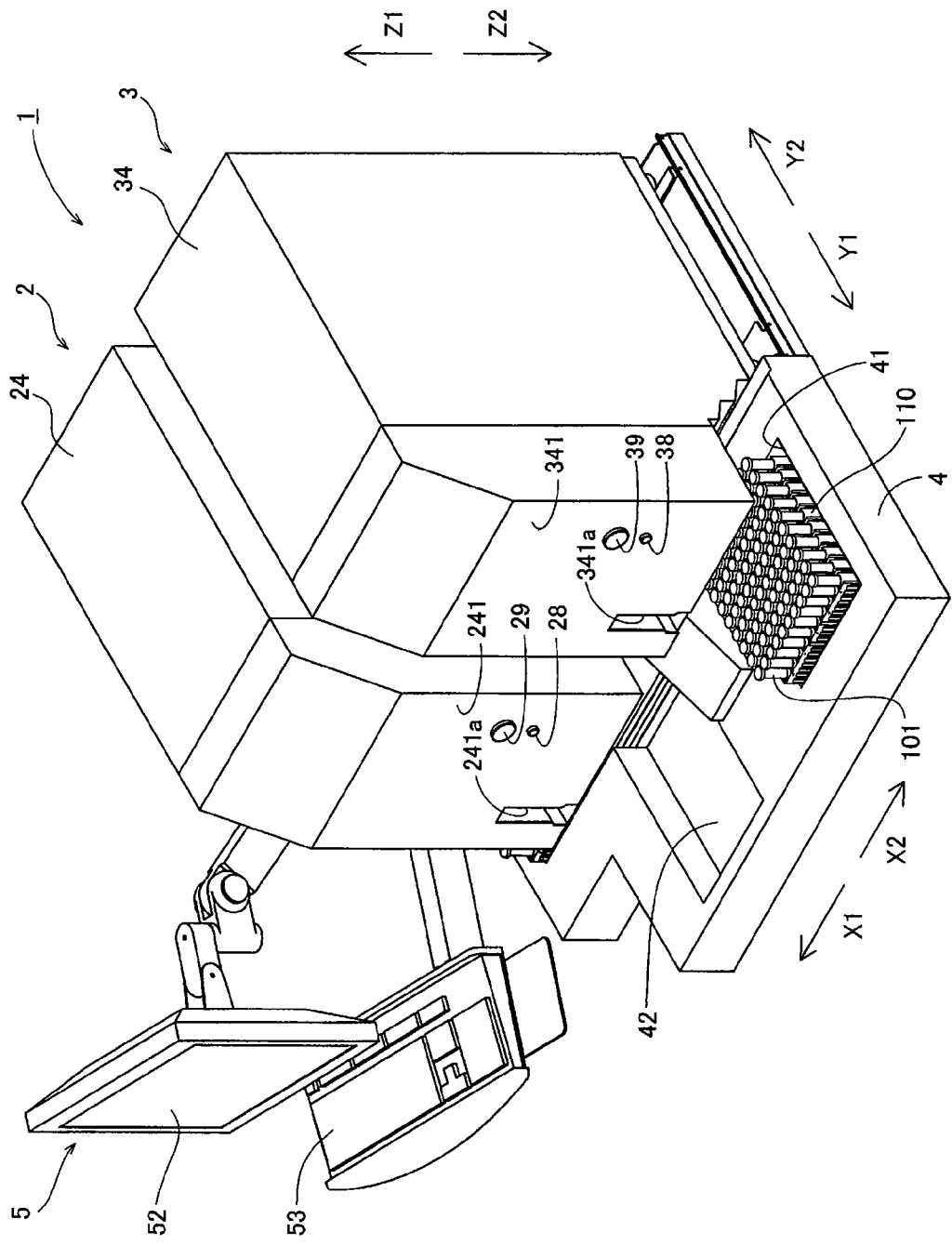
FIG. 1 is a perspective view showing an overall configuration of a blood analyzer according to one embodiment of the present invention.

FIG. 1 is a perspective view showing an overall configuration of a blood analyzer according to one embodiment of the present invention. FIGS. 2 to 19 are views describing the details of each unit of the blood analyzer according to one embodiment shown in FIG. 1. First, the overall configuration of the blood analyzer 1 according to one embodiment of the present invention will be described with reference to FIGS. 1 to 19. In the present embodiment, a case in which the present invention is applied to the blood analyzer serving as one example of the analyzer will be described.

Figure 5:
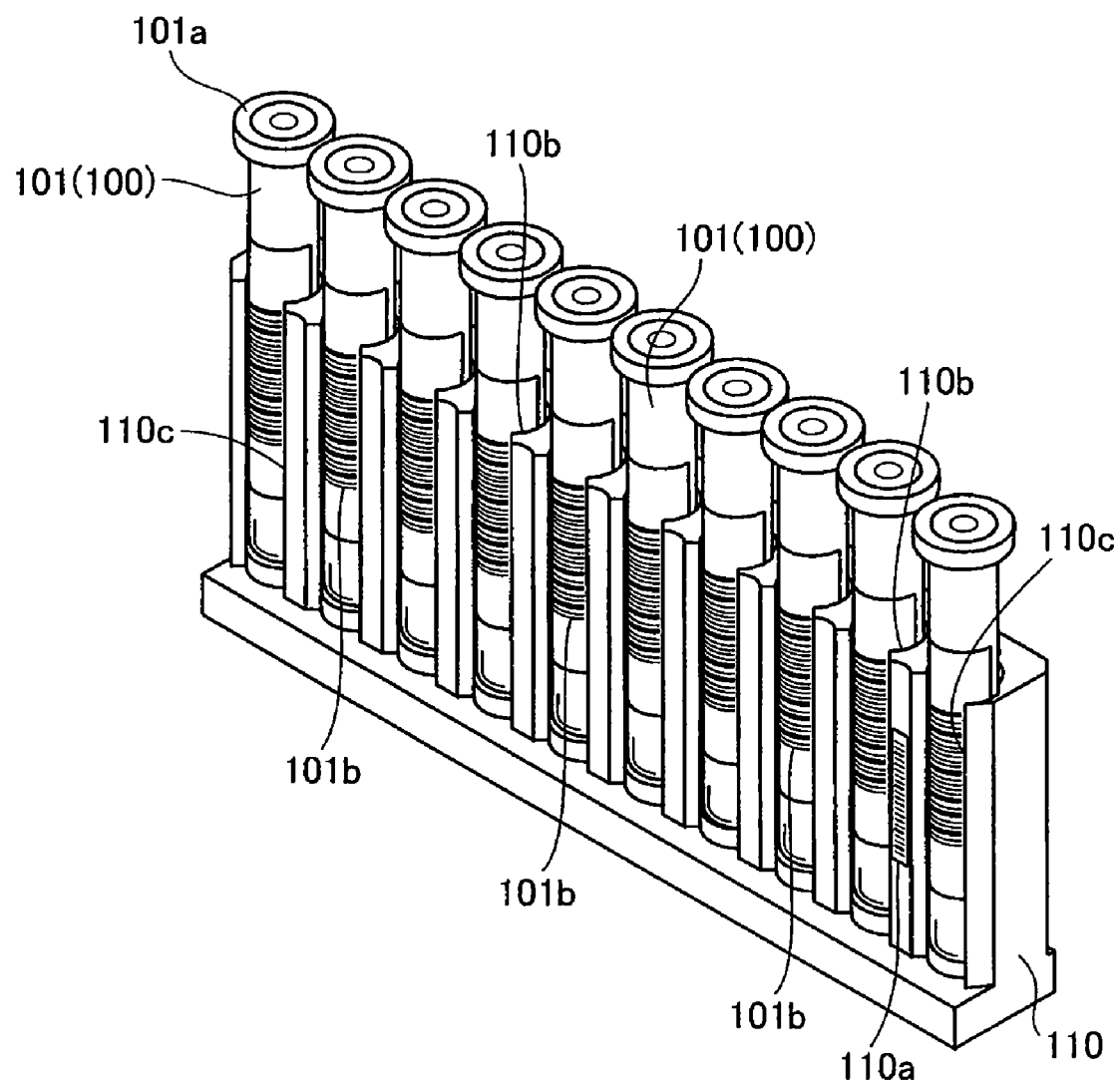
FIG. 5 is a perspective view showing a rack and a long vial of the blood analyzer according to one embodiment shown in FIG. 1.
Figure 6:
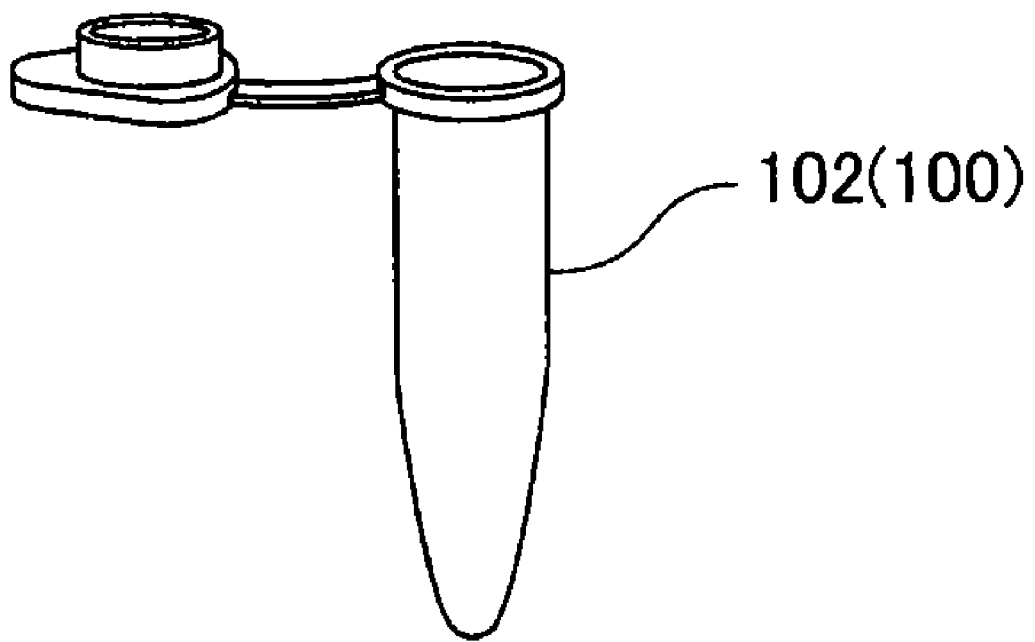
FIG. 6 is a perspective view showing a microtube of the blood analyzer according to one embodiment shown in FIG. 1.

In the present embodiment, as shown in FIGS. 5 and 6, a sample container 100 for accommodating blood, which is a specimen, includes a long vial 101 (see FIG. 5), which is a specimen container of a vertically long shape, having a rubber sealing lid 101a, and a microtube 102 (see FIG. 6), which is a specimen container for mainly accommodating a small amount of specimen, smaller than the long vial 101. In the description of the present embodiment, description is made using "sample container 100" to include both the long vial 101 and the microtube 102 when corresponding to both the long vial 101 and the microtube 102, and description is made using the "long vial 101" or the "microtube 102" when corresponding to only one of the long vial 101 or the microtube 102.

Figure 2:
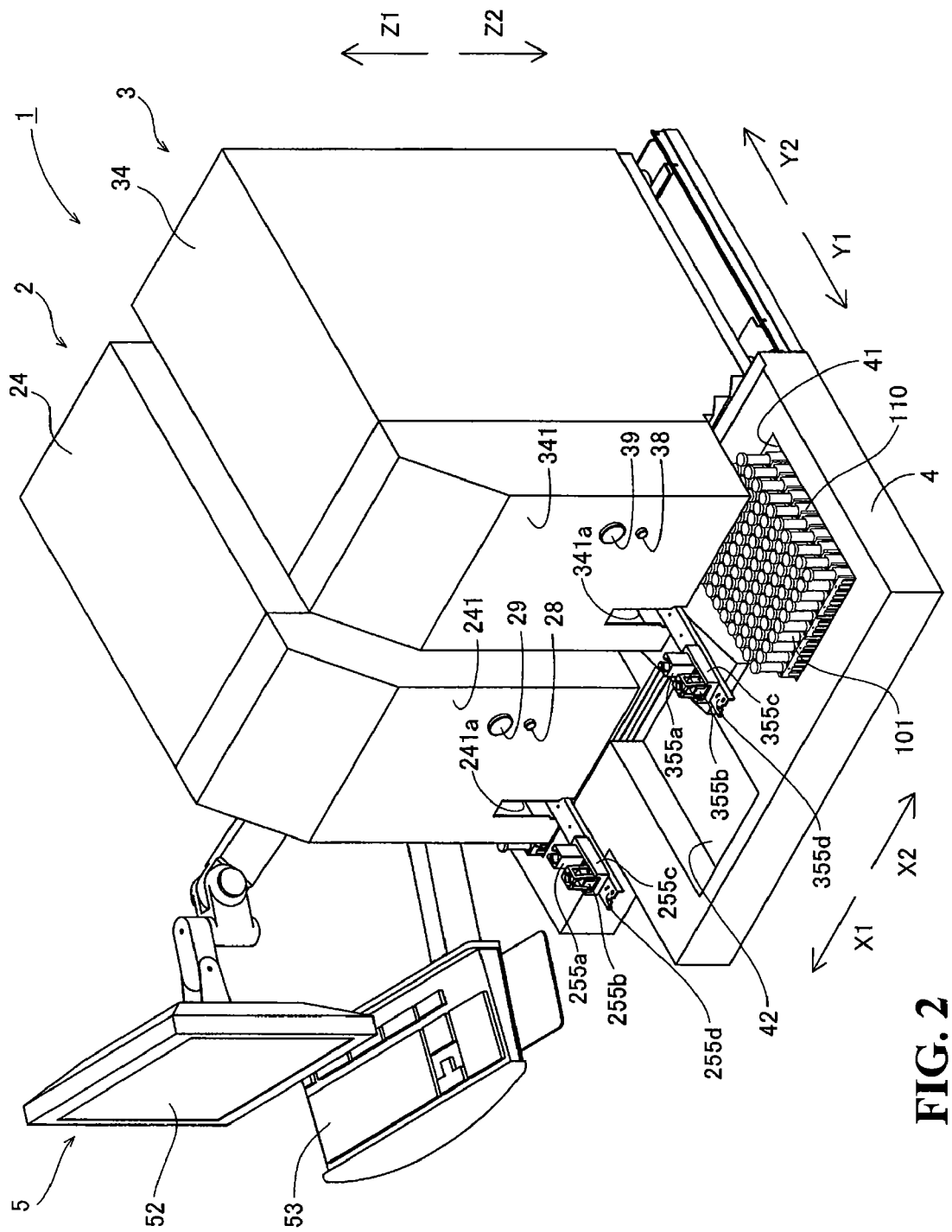
FIG. 2 is a perspective view describing details of each unit of the blood analyzer according to one embodiment shown in FIG. 1.

As shown in FIGS. 1 and 2, the blood analyzer 1 according to the present embodiment includes two measurement units, first measurement unit 2 and second measurement unit 3, a specimen conveying device (sampler) 4 arranged on the front surface side (side on direction of arrow Y1) of the first measurement unit 2 and the second measurement unit 3, and a control device 5 including a PC (personal computer) electrically connected to the first measurement unit 2, the second measurement unit 3, and the specimen conveying device 4. The blood analyzer 1 is connected to a host computer 6 (see FIG. 3) by the control device 5.

Figure 3:
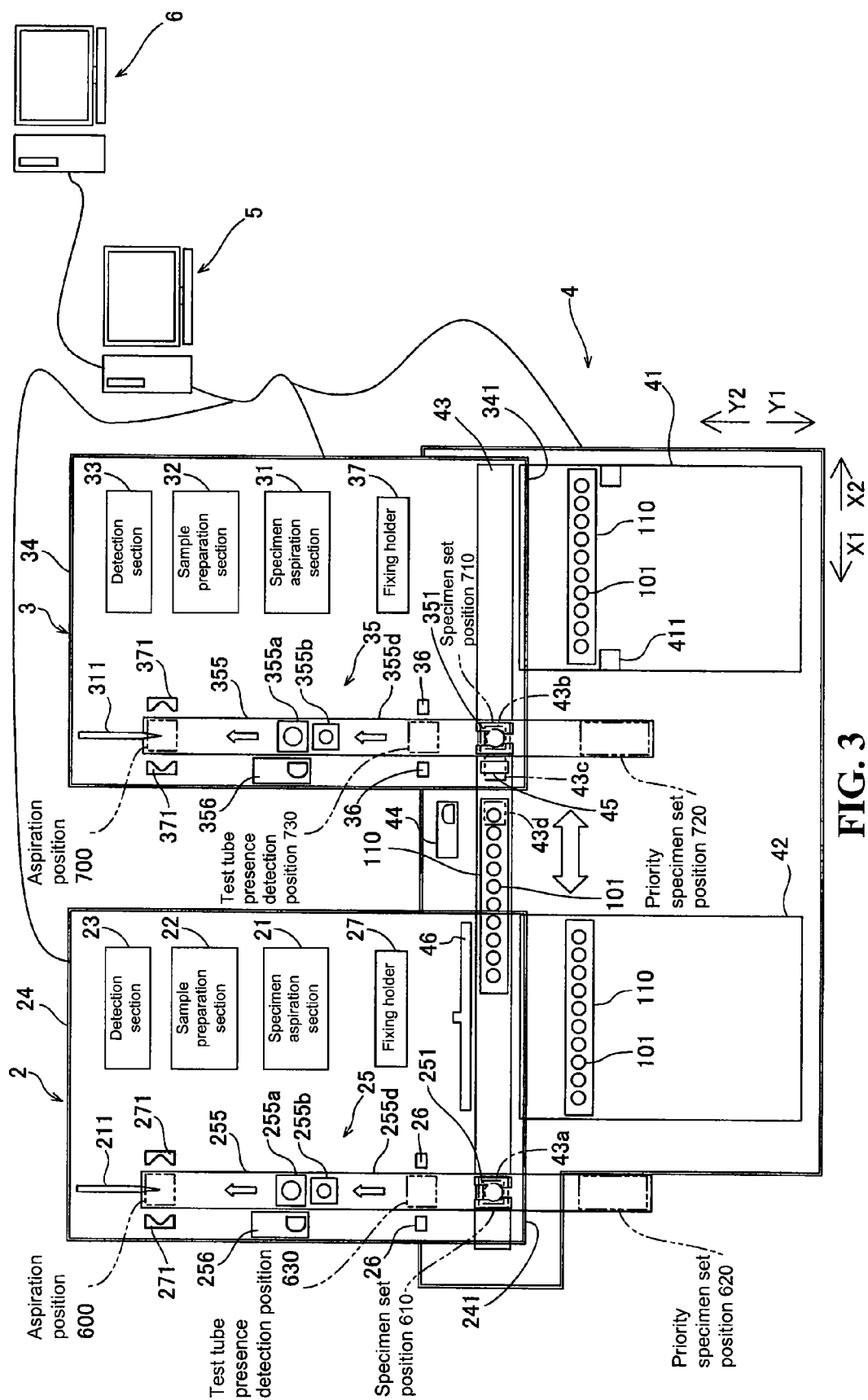
FIG. 3 is a schematic view showing a measurement unit and a specimen conveying device of the blood analyzer according to one embodiment shown in FIG. 1.

As shown in FIGS. 1 to 4, the first measurement unit 2 and the second measurement unit 3 are measurement units of substantially the same type, and are arranged adjacent to each other. Specifically, in the present embodiment, the second measurement unit 3 measures the specimen for the same measurement item by using the same measurement principle as the first measurement unit 2. Furthermore, the second measurement unit 3 performs measurement on the measurement item that is not analyzed by the first measurement unit 2. As shown in FIG. 3, the first measurement unit 2 and the second measurement unit 3 respectively include specimen aspiration sections 21, 31 for aspirating the blood, which is the specimen, from a sample container (test tube) 100, sample preparation sections 22, 32 for preparing the detection sample from the blood aspirated by the specimen aspiration sections 21, 31, and detection sections 23, 33 for detecting the blood cells of the blood from the detection sample prepared by the sample preparation sections 22, 32.

Each of the first measurement unit 2 and the second measurement unit 3 also includes unit covers 24, 34 for interiorly accommodating the specimen aspiration sections 21, 31 and the sample preparation sections 22, 32; sample container conveying sections 25, 35 for retrieving the sample container 100 inside the unit covers 24, 34 and conveying the sample container 100 to aspiration positions 600, 700 (see FIG. 3) by the specimen aspiration sections 21, 31; presence detection sections 26, 36 for detecting the presence of the long vial 101 conveyed to the inside by the sample container conveying sections 25, 35; and fixing holders 27, 37 for fixedly holding the long vial 101 at the aspiration positions 600 and 700 (see FIG. 3). As shown in FIGS. 1 and 2, on the outer surface of front surface portions 241, 341 of the unit covers 24, 34, specimen setting portion open/close buttons 28, 38, priority specimen measurement start buttons 29, 39, and openings 241*a*, 341*a* through which movement portions 255*d*, 355*d*, to be hereinafter described, of the sample container conveying sections 25, 35 pass are respectively arranged.

Figure 7:
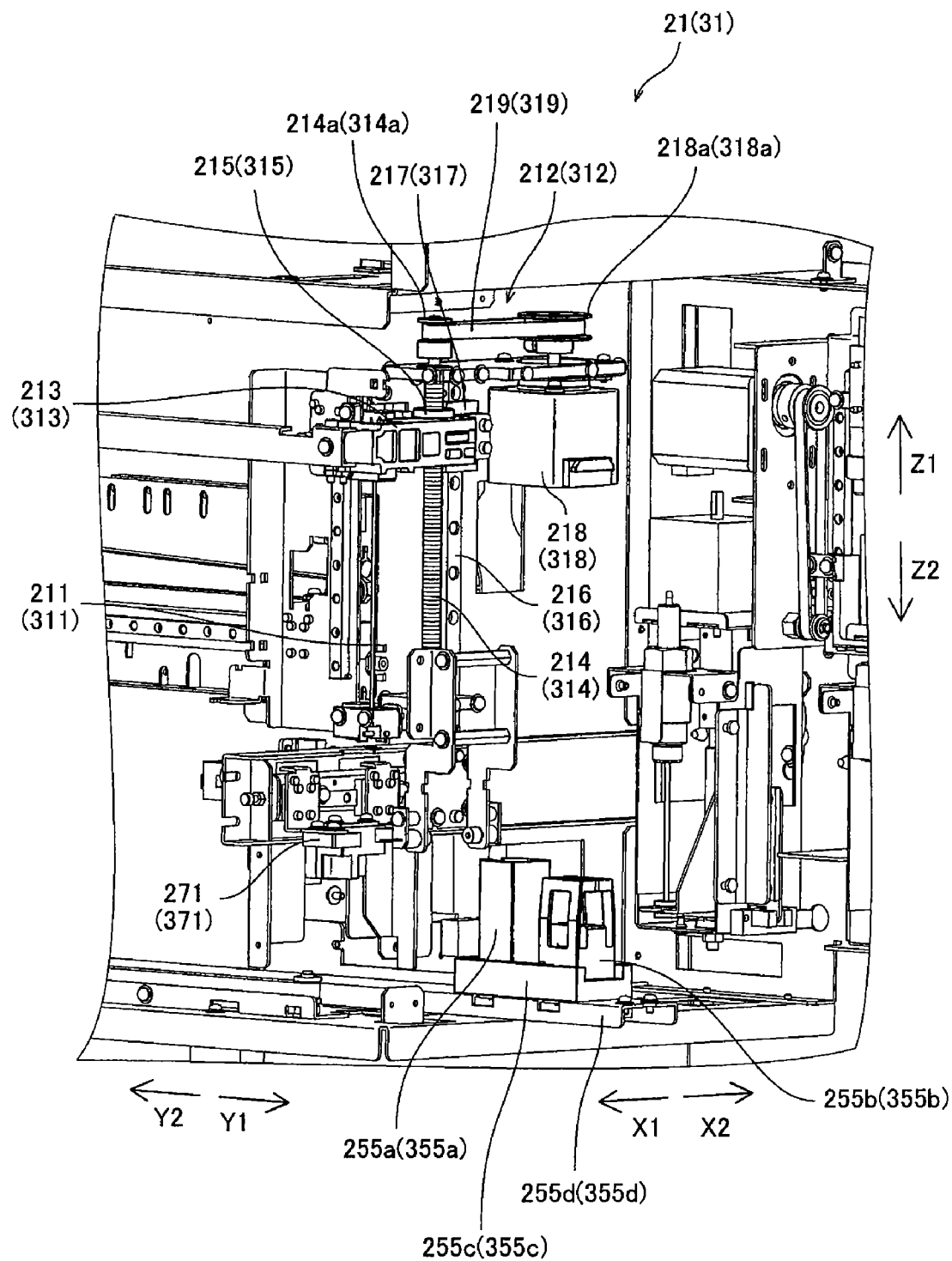
FIG. 7 is a perspective view showing the vicinity of a specimen aspiration section of the blood analyzer according to one embodiment shown in FIG. 1.

As shown in FIG. 7, the specimen aspiration sections 21 and 31 include pipettes 211 and 311, and pipette movement portions 212, 312, respectively. The pipettes 211 and 311 have the distal ends formed such that the sealing lid 101*a* (see FIG. 5), to be hereinafter described, of the long vial 101 can be passed through. The pipette movement portions 212 and 312 have a function of moving the pipettes 211 and 311 in a vertical direction (direction of arrows Z1 and Z2), respectively. The pipette movement portions 212 and 312 have horizontal arms 213, 313 for fixedly holding the pipettes 211, 311, screw shafts 214, 314 passing through the horizontal arms 213, 313 in the vertical direction (direction of arrows Z1 and Z2), and nut 215, 315 to be screwed to the screw shafts 214, 314, respectively. Furthermore, the pipette movement portions 212 and 312 each has slide rails 216, 316 arranged parallel (direction of arrows Z1 and Z2) to the screw shafts 214, 314, slidable members 217, 317 slidably attached to the slide rails 216, 316, and stepping motors 218, 318. The horizontal arms 213, 313 are fixed to the nuts 215, 315 and the slidable members 217, 317, respectively.

Pulleys 214*a*, 314*a* are attached to the upper ends of the screw shafts 214, 314, respectively. Pulleys 218*a*, 318*a* are attached to output shafts of the stepping motors 218, 318, respectively. Annularly formed timing belts 219, 319 are turnably stretched between the pulleys 214*a*, 314*a* and the pulleys 218*a*, 318*a*. The rotational drive of the stepping motor 218 (318) is transmitted to the screw shaft 214 (314) via the timing belt 219 (319) to thereby rotate the screw shaft 214 (314), so that the horizontal arm 213 (313) moves in the vertical direction (direction of arrows Z1 and Z2). The pipette 211 (311) is moved in the vertical direction (direction of arrows Z1 and Z2) with the movement in the vertical direction (direction of arrows Z1 and Z2) of the horizontal arm 213 (313).

The stepping motor 218 (318) is configured to be able to fluctuate the rotary torque according to the supplied current value (magnitude of drive pulse). The stepping motor 218 (318) is configured to lose synchronism when a load of greater than or equal to the rotary torque of the motor is applied. Specifically, the stepping motor 218 (318) is controlled such that the rotary torque becomes small when aspirating the blood accommodated in the microtube 102 (see FIG. 6) compared to when aspirating the blood accommodated in the long vial 101 (see FIG. 5), and is configured to lose synchronism when the distal end of the pipette 211 (311) contacts the bottom portion of the microtube 102. Thus, the microtube 102 can be prevented from being damaged even if the distal end of the pipette 211 (311) contacts the bottom portion of the microtube 102. The specimen accommodated in the microtube 102 of small accommodation capacity can be aspirated barely without waste by the specimen aspiration section 21 (31) by causing the distal end of the pipette 211 (311) to reach the bottom portion of the microtube 102.

When aspirating the blood accommodated in the long vial 101 of larger accommodation capacity than the microtube 102, the stepping motor 218 (318) is controlled to lower the pipette 211 (311) at a predetermined rotary torque, and after the pipette 211 (311) passes through the sealing lid 101*a*, to lower the pipette until the distal end reaches the vicinity of the bottom portion of the long vial 101. In this case, the pipette 211 (311) stops the movement immediately before the distal end contacts the bottom portion of the long vial 101, unlike to the case of the microtube 102. Thus, when aspirating the blood accommodated in the long vial 101, the pipette 211 (311) does not contact the bottom portion of the long vial 101, and thus the long vial 101 is not damaged by the pipette 211 (311). The stepping motor 218 (318) is configured such that the rotation speed fluctuates according to the frequency of the drive pulse.

The detection sections 23 and 33 are configured to perform RBC detection (detection of red blood cells) and PLT detection (detection of platelet) through the sheath flow DC detection method, and perform HGB detection (detection of blood pigment in blood) through the SLS-hemoglobin method. The detection sections 23 and 33 are also configured to perform WBC detection (detection of white blood cells) through the flow cytometry method using a semiconductor laser.

The detection results obtained in the detection sections 23 and 33 are transmitted to the control device 5 as measurement data (measurement result) of the specimen. The measurement data is data that serves as the final analysis result (number of red blood cells, number of platelets, hemoglobin amount, number of white blood cells, and the like) provided to the user.

Figure 4:
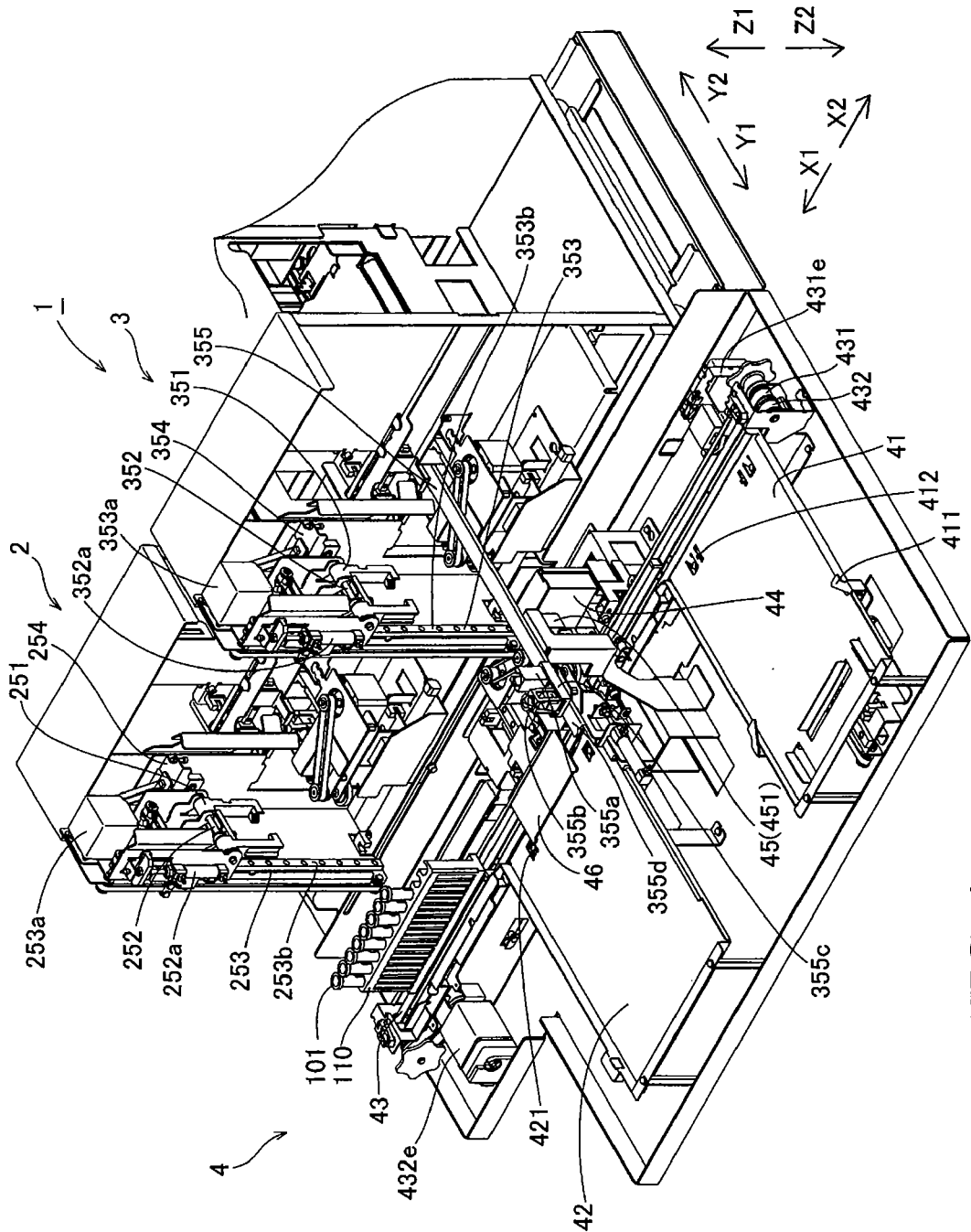
FIG. 4 is a perspective view showing the measurement unit and the specimen conveying device of the blood analyzer according to one embodiment shown in FIG. 1.

As shown in FIG. 4, the sample container conveying sections 25 and 35 include, hand portions 251, 351 capable of gripping the long vial 101, open/close portions 252, 352 for opening/closing the hand portions 251, 351 so as to grip the long vial 101, vertical movement portions 253, 353 for linearly moving the hand portions 251, 351 in the vertical direction (direction of arrows Z1 and Z2), and stirring portion 254, 354 for moving the hand portions 251, 351 in a pendulum-form in the vertical direction (direction of arrows Z1 and Z2), respectively. Furthermore, the sample container conveying sections 25 and 35 include sample container transfer sections 255, 355 for substantially horizontally moving the sample container 100 in the directions of the arrows Y1 and Y2, and barcode readers 256, 356, respectively, as shown in FIG. 3.

The hand portion 251 (351) is arranged on the upper side of the conveyance path of a rack 110 conveyed by the specimen conveying device 4. The hand portions 251 and 351 are each configured to move downward (direction of arrow Z2) when the long vial 101 is conveyed to a first provision 43a and a second provision position 43b (see FIG. 3), to be hereinafter described, by the specimen conveying device 4, and then to be opened/closed by the open/close portions 252, 352 to grip the long vial 101 accommodated in the rack 110. In this case, the movement portion 255d (355d), to be hereinafter described, of the sample container transfer section 255 (355) is accommodated on the back side (side on direction of arrow Y2) than the front surface portion 241 (341) of the unit cover 24 (34), and thus the movement to the lower side of the hand portion 251 (351) is not inhibited.

The hand portion 251 (351) is configured to take out the gripped long vial 101 from the rack 110 by moving to the upper side (direction of arrow Z1), and thereafter, to be moved (e.g., ten rounds) in the pendulum-form by the stirring portion 254 (354). The hand portion 251 (351) thus can stir the blood in the gripped long vial 101. After terminating the stirring, the hand portion 251 (351) moves to the lower side (direction of arrow Z2), and releases the gripping of the long vial 101 by the open/close portion 252 (352). Specifically, the hand portion 251 (351) is configured to set the long vial 101 at a first specimen setting portion 255a (355a) moved to the specimen set position 610 (710) (see FIG. 3) by the sample container transfer section 255 (355). The hand portion 251 (351) thus can transfer the long vial 101 from the rack 101 to the first specimen setting portion 255a (355a) by moving the long vial 101 in the up and down directions (direction of arrows Z1 and Z2) at substantially the same position in plan view. As shown in FIG. 3, in plan view, the first provision position 43a and the specimen set position 610 are arranged to overlap, and the second provision position 43b and the specimen set position 710 are arranged to overlap.

The above operation of taking out the long vial 101 from the rack 110 conveyed by the specimen conveying device 4, and setting the same in the first specimen setting portion 255a (355a) is executed by controlling the stepping motor 253a (353a) for moving the hand portion 251 (351) up and down, a stepping motor 431e for driving a first belt 431, and a stepping motor 432e for driving a second belt 432 (see FIG. 4) by the CPU 51a to be hereinafter described.

In other words, the CPU 51a first executes the process of conveying the long vial 101 to the first provision position 43a (43b) by the specimen conveying device 4. When the movement portion 255d (355d) is not present on the upper side of the first provision position 43a (43b), the CPU 51a executes the process of gripping the long vial 101 by means of the hand portion 251 (351), raising the long vial 101 until the lower end of the long vial 101 is positioned on the upper side than the upper end face of the first specimen setting portion 255a (355a), and stirring the long vial 101. The CPU 51a then executes the process of moving the movement portion 255d (355d) until the first specimen setting portion 255a (355d) is positioned immediately below the raised long vial 101. The CPU 51a executes the process of lowering the hand portion 251 (351) and releasing the gripping to set the long vial 101 in the first specimen setting portion 255a (355d). The CPU 51a then executes the process of moving the movement portion 255d (355d) until the long vial 101 set in the first specimen setting portion 255a (355d) is positioned at the aspiration position 600 (700).

The open/close portion 252 (352) is configured to open/close the hand portion 251 (351) so as to grip the long vial 101 by the power of the air cylinder 252a (352a).

The vertical movement portion 253 (353) is configured to move the hand portion 251 (351) in the vertical direction (direction of arrows Z1 and Z2) along the rail 253b (353b) by the power of the stepping motor 253a (353a).

The stirring portion 254 (354) is configured to move the hand portion 251 (351) in the pendulum-form in the vertical direction (direction of arrows Z1 and Z2) by the power of a stepping motor (not shown).

Figure 8:
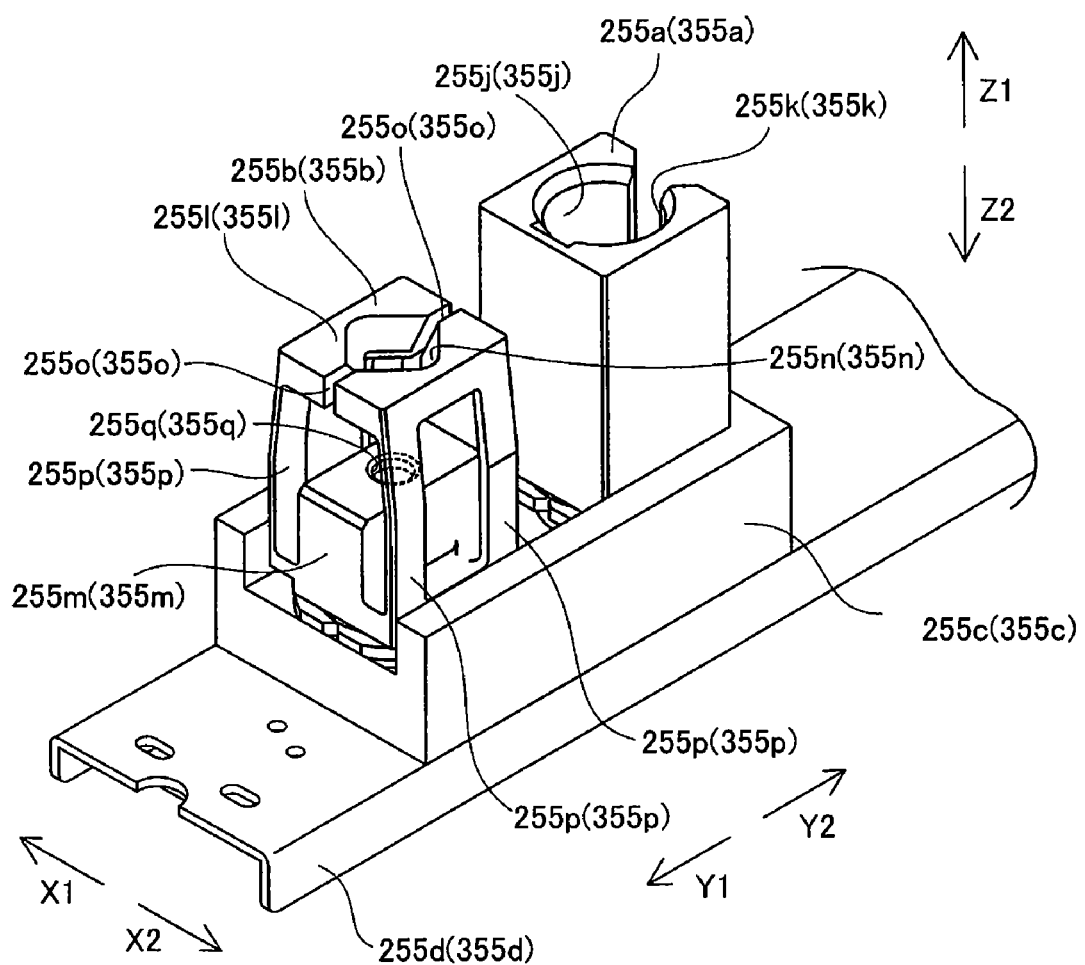
FIG. 8 is a perspective view showing a specimen setting portion of the blood analyzer according to one embodiment shown in FIG. 1.
Figure 9:
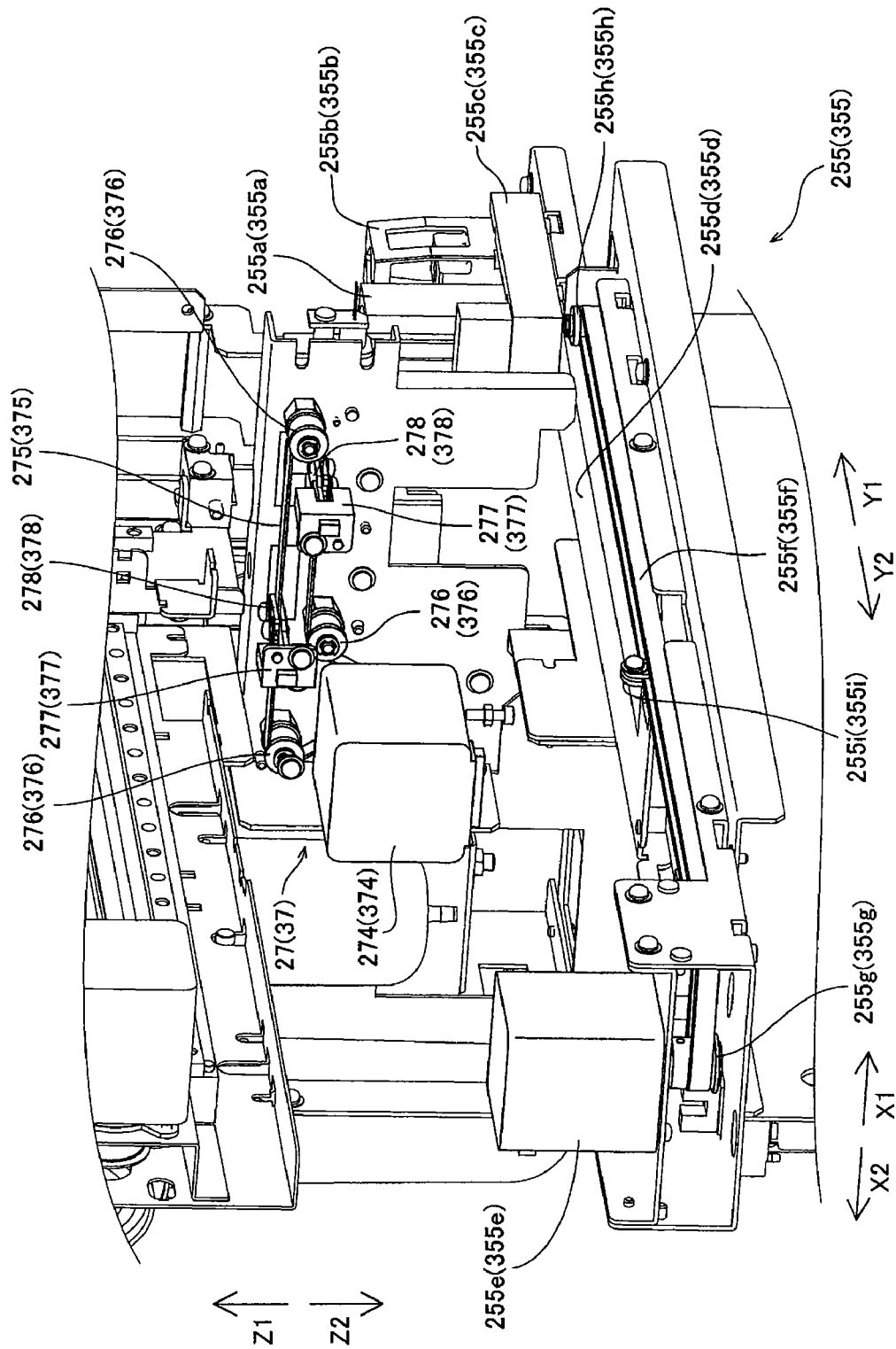
FIG. 9 is a perspective view showing the vicinity of a sample container transfer section and a fixing holder of the blood analyzer according to one embodiment shown in FIG. 1.

As shown in FIGS. 8 and 9, sample container transfer sections 255 and 355 include the first specimen setting portions 255a, 355a, the second specimen setting portions 255b, 355b arranged on the front side (side on direction of arrow Y1) than the first specimen setting portions 255a, 355a, the movement portions 255d, 355d attached with such two specimen setting portions by way of the adapters 255c, 355c, the stepping motors 255e, 355e (see FIG. 9), and the annular timing belts 255f, 355f (see FIG. 9), respectively.

As shown in FIG. 9, pulleys 255g and 355g are attached to the output shaft of the stepping motors 255e and 355e, respectively. The timing belts 255f and 355f are turnably stretched respectively by the pulleys 255g, 355g and the pulleys 255h, 355h arranged on the front side (side on direction of arrow Y1) than the stepping motors 255e, 355e. Thus, when the stepping motor 255e (355e) is rotatably driven, the timing belt 255f (355f) is turned between the pulley 255g (355g) and the pulley 255h (355h). Part of the timing belt 255f (355f) is arranged to extend in the front and back direction (direction of arrows Y1 and Y2), and the movement portion 255d (355d) is attached to the portion arranged to extend in the front and back directions of the timing belt 255f (355f) by an attachment 255i (355i) near the back end. The movement portion 255d (355d) then can be moved in the front and back directions (direction of arrows Y1 and Y2) with the turning of the timing belt 255f (355f).

The first specimen setting portion 255a (355a) attached to the movement portion 255d (355d) and the second specimen setting portion 255b (355b) can be moved to a predetermined position corresponding to the operation of the measurement process by controlling the rotational drive of the stepping motor 255e (355e). Specifically, each of specimen setting portions can be arranged at the aspiration positions 600, 700, the specimen set positions 610, 710, the priority specimen set positions 620, 720, and the test tube presence detection positions 630, 730 shown in FIG. 3 by the sample container transfer sections 255, 355. As shown in FIG. 3, each position above is on the movement path of the specimen setting portion in the order of, from the front side (side on direction of arrow Y1) of the blood analyzer 1, the priority specimen set position 620 (720) arranged on the front side than the front surface portion 241 (341) of the unit cover 24 (34), the specimen set position 610 (710) arranged on the back side (side on direction of arrow Y2) than the front surface portion 241 (341), the test tube presence detection position 630 (730), and the aspiration position 600 (700).

Figure 10:
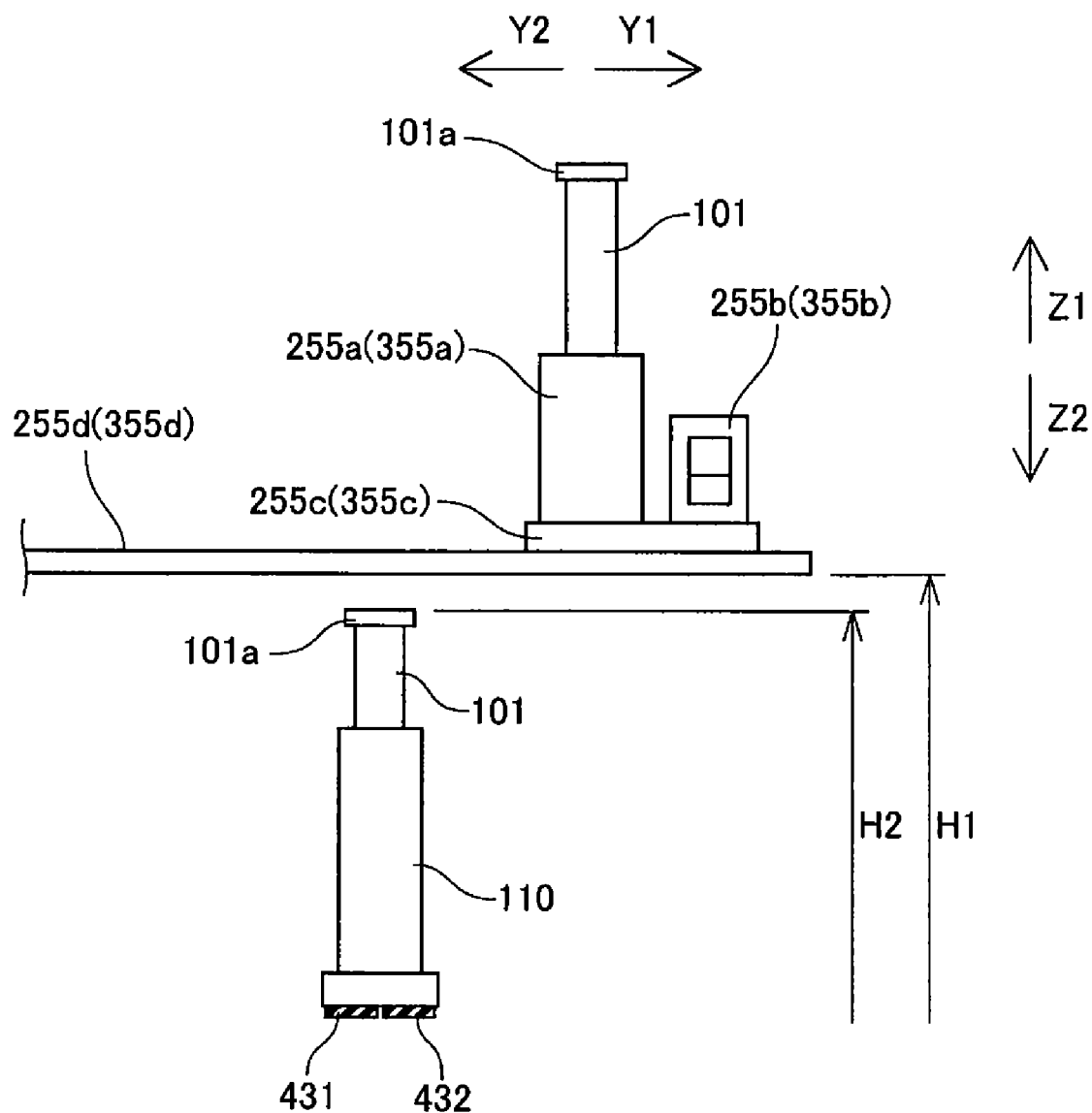
FIG. 10 is a view describing the position of the movement portion of the blood analyzer according to one embodiment shown in FIG. 1.

In the present embodiment, as shown in FIG. 3, the sample container transfer section 255 (355) is configured to, in plan view, pass the upper side of the conveyance path of the rack 110 and move each specimen setting portion to a predetermined position so that the movement portion 255d (355d) is orthogonal to the conveyance path of the rack 110 conveyed by the specimen conveying device 4. Specifically, as shown in FIG. 10, the movement portion 255d (355d) is arranged at a position H1 higher than an upper end position H2 of the rack 110 conveyed by the specimen conveying device 4, and is configured to be moved in the front and back directions (direction of arrows Y1 and 2) at substantially the horizontal direction. Each specimen setting portion attached to the movement portion 255d (355d) then can be conveyed to the predetermined position while continuing the conveying operation of the rack 110 by the specimen conveying device 4.

The first specimen setting portions 255a, 355a have holding holes 255h, 355j, respectively, as shown in FIG. 8, wherein the long vial 101 (see FIG. 5) can be held in the holding holes 255j, 355j. Cutouts 255k, 355k are formed at the side surface on the back side (side on direction of arrow Y2) of the first specimen setting portions 255a, 355a so that the rear side (side on direction of arrow Y2) of the holding holes 255j, 355j is opened. Thus, the barcode 101b (see FIG. 5b) attached to the long vial 101 can be visually recognized from the outer side with the long vial 101 held in the first specimen setting portion 255a (355a). The first specimen setting portion 255a (355a) is removably attached to the adapter 255c (355c), and can be changed with other first specimen setting portion depending on the type of the long vial 101.

The second specimen setting portions 255b, 355b have upper holders 255l, 355l and lower holders 255m, 355m, respectively. The second specimen setting portion 255b (355b) holds the upper side of the microtube 102 (see FIG. 6) by the upper holder 255l (355l), and holds the lower side of the microtube 102 (see FIG. 6) by the lower holder 255m (355m), so that the microtube 102 is held at two locations of different lengths, and thus can be held in a stable state. The upper holders 255l, 355l are formed with holding holes 255n, 355n, respectively, and separating portions 255o, 355o for dividing the upper holders 255l, 355l into two in the left and right directions (directions of arrow X1 and X2) are formed at the front and back portions of the holding holes 255n, 355n. The portion divided into two in the left and right direction is supported by two supporting portions 255p, 355p elastically deformable to the outer side direction, respectively. Thus, if the supporting portion 255p (355p) for supporting the portion divided into two in the left and right directions is bent in the outer side direction, the inner diameter of the holding hole 255n (355n) can be changed, and as a result, a plurality of types of microtubes 102 having different size can be held.

The lower holders 255m, 355m have holding holes 255q, 355q at a position corresponding to the position of the holding holes 255n, 355n of the upper holders 255l, 355l in plan view, and hold the lower side of the microtube 102 with the lower end of the microtube 102 inserted in the holding holes 255q, 355q, respectively. Furthermore, the second specimen setting portion 255b (355b) is removably attached to the adapter 255c (355c), and can be changed with other second specimen setting portion so as to respond to the microtube 102 of the type that cannot be responded with the flexural deformation of the supporting portion 255p (355p).

The barcode reader 256 (356) is configured to read the barcode 101b attached to each long vial 101, as shown in FIG. 5. The barcode reader 256 (356) is also configured to read the barcode 101 while rotating the target long vial 101 in the horizontal direction by a rotating device (not shown) while being held at the first specimen setting portion 255a (355a). Even if the barcode 101 b of the long vial 101 is attached to the opposite side with respect to the barcode reader 256 (356), the barcode 101b can be directed to the barcode reader 256 (356) side by rotating the long vial 101. The barcode 101b of each long vial 101 is uniquely attached to each specimen, and is used to manage the analysis result of each specimen, and the like.

Figure 11:
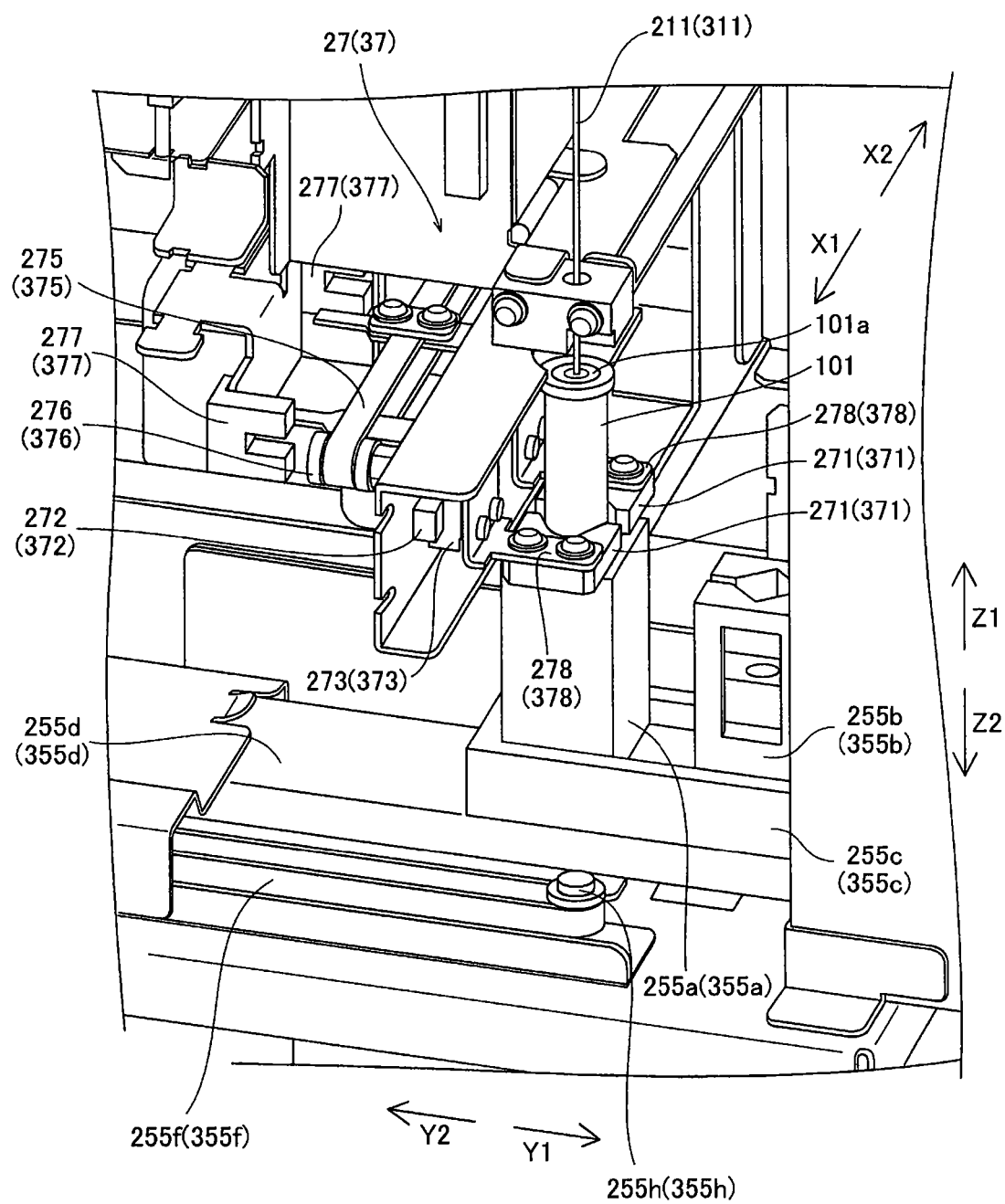
FIG. 11 is a perspective view showing the vicinity of a fixing holder of the blood analyzer according to one embodiment shown in FIG. 1.
Figure 12:
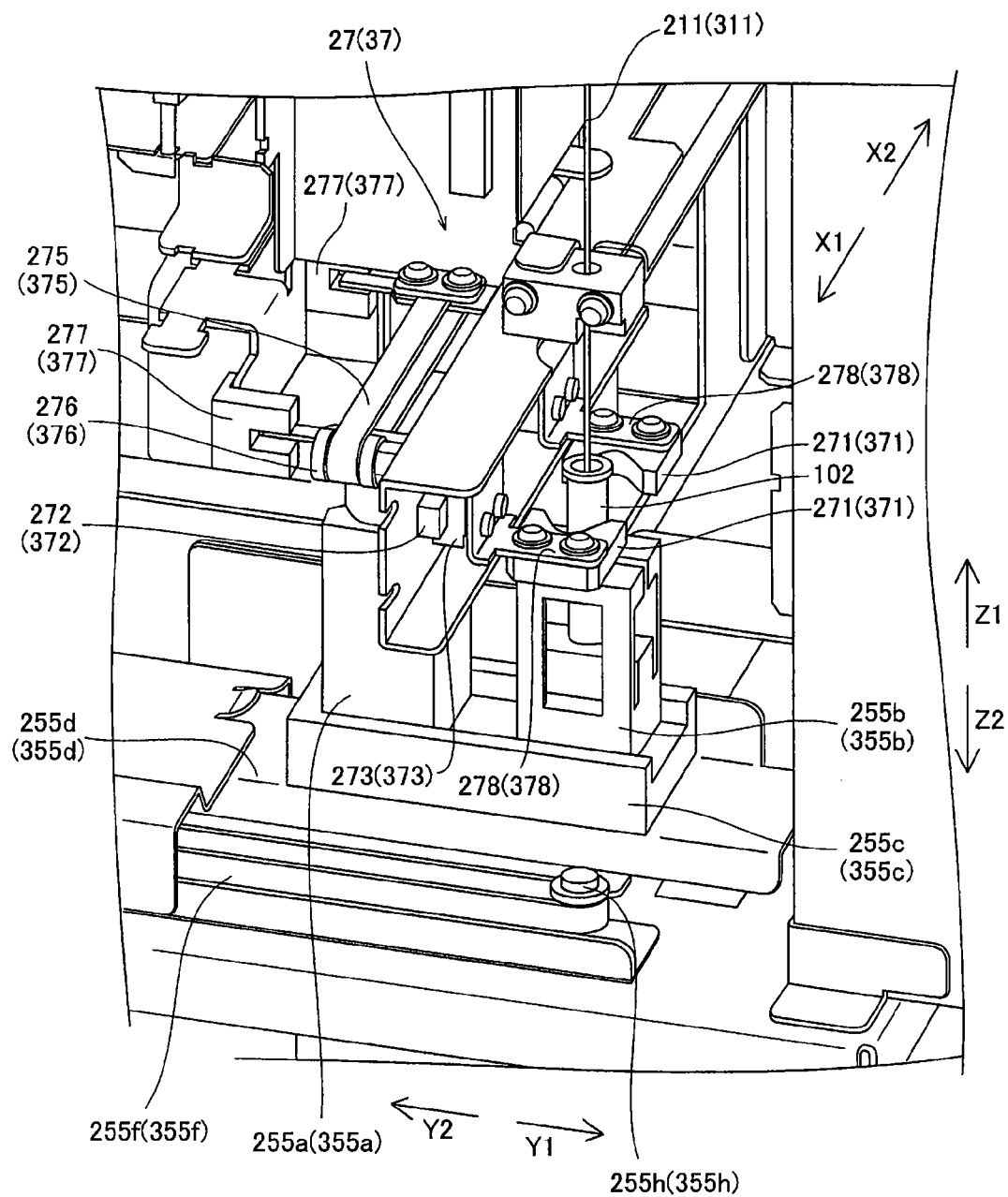
FIG. 12 is a perspective view showing the vicinity of the fixing holder of the blood analyzer according to one embodiment shown in FIG. 1.

As shown in FIG. 11, the fixing holder 27 (37) is configured to fixedly hold the long vial 101 transferred to the aspiration position 600 (700). As shown in FIG. 12, the fixing holder 27 (37) is configured not to fixedly hold with respect to the microtube 102 transferred to the aspiration position 600 (700). When using the microtube 102, the microtube 102 is stably held using the flexural deformation of the supporting portion 255p (355p) of the second specimen setting portion 255b (355b), as described above, and thus the fixing holder 27 (37) does not need to be used. The fixing holders 27 and 37 have a pair of sandwiching parts 271, 371, slide rails 272, 372 arranged to extend horizontally in the direction of arrows X1 and X2, and slidable members 273, 373 slidably attached to the slide rails 272, 372, respectively, as shown in FIGS. 11 and 12. Furthermore, the fixing holders 27, 37 have stepping motors 274, 374, annular timing belts 275, 375, a plurality of pulleys 276, 376, and position sensors 277, 377, respectively, as shown in FIG. 9.

As shown in FIGS. 11 to 14, the pair of sandwiching parts 271, 371 has the opposing side surfaces formed to a substantially V-shape in plan view, so that the long vial 101 of different size, outer shape, and the like can be responded. As shown in FIGS. 11 and 12, the pair of sandwiching parts 271 (371) is attached to the slidable member 273 (373) and is also attached to the timing belt 275 (375) by the coupling part 278 (378). Thus, the pair of sandwiching parts 271 (371) are moved in the horizontal direction integral with the slidable member 273 (373) with the turning of the timing belt 275 (375). The annular timing belt 275 (375) is configured to turn while being guided by the plurality of pulleys 276 (376) when the stepping motor 274 (374) is rotationally driven. As shown in FIG. 9, the annular timing belt 275 (375) is turnably stretched so as to be a predetermined shape by the plurality of pulleys 276 (376). Specifically, the timing belt 275 (375) is formed to two upper and lower stages by folding back the portion arranged extending horizontally in the directions of the arrows X1 and X2 by the pulley 276 (376). Thus, when the timing belt 275 (375) is turned, the upper portion and the lower portion of the two upper and lower stages are moved in opposite directions, directions of arrows X1 and X2, with respect to each other.

Figure 13:
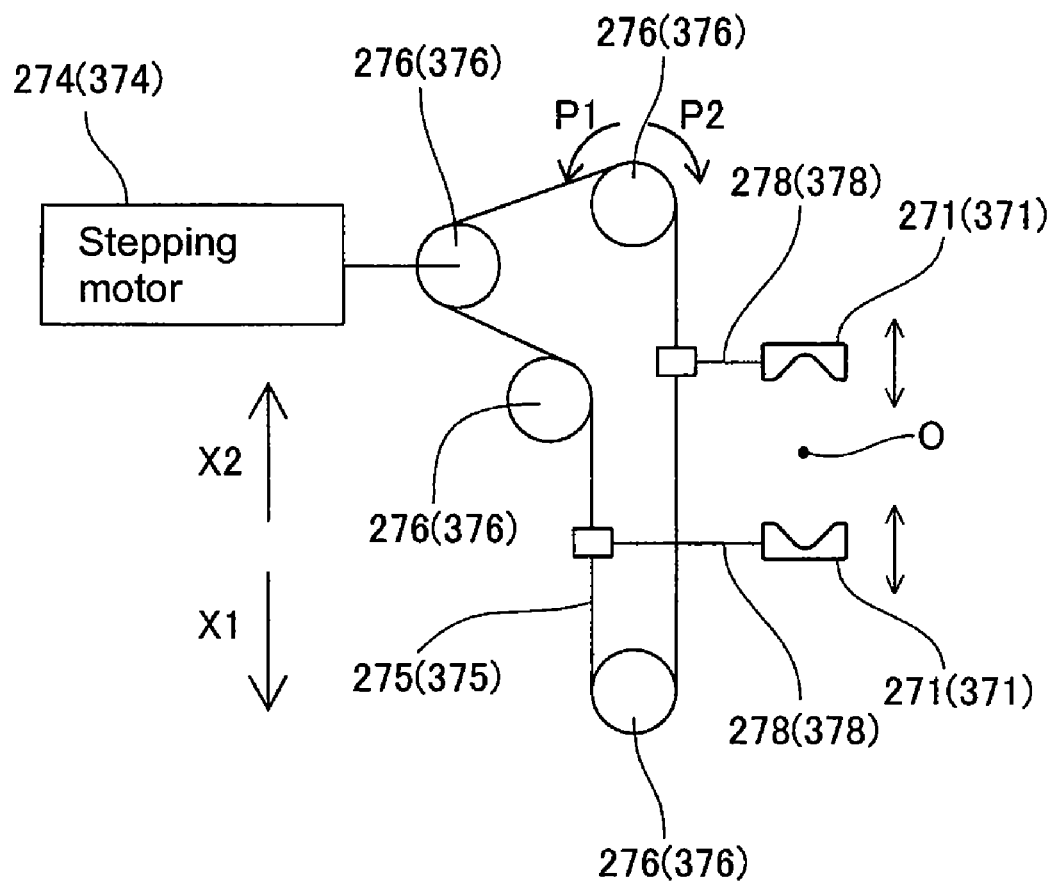
FIG. 13 is view describing a configuration of the fixing holder of the blood analyzer according to one embodiment shown in FIG. 1.
Figure 14:
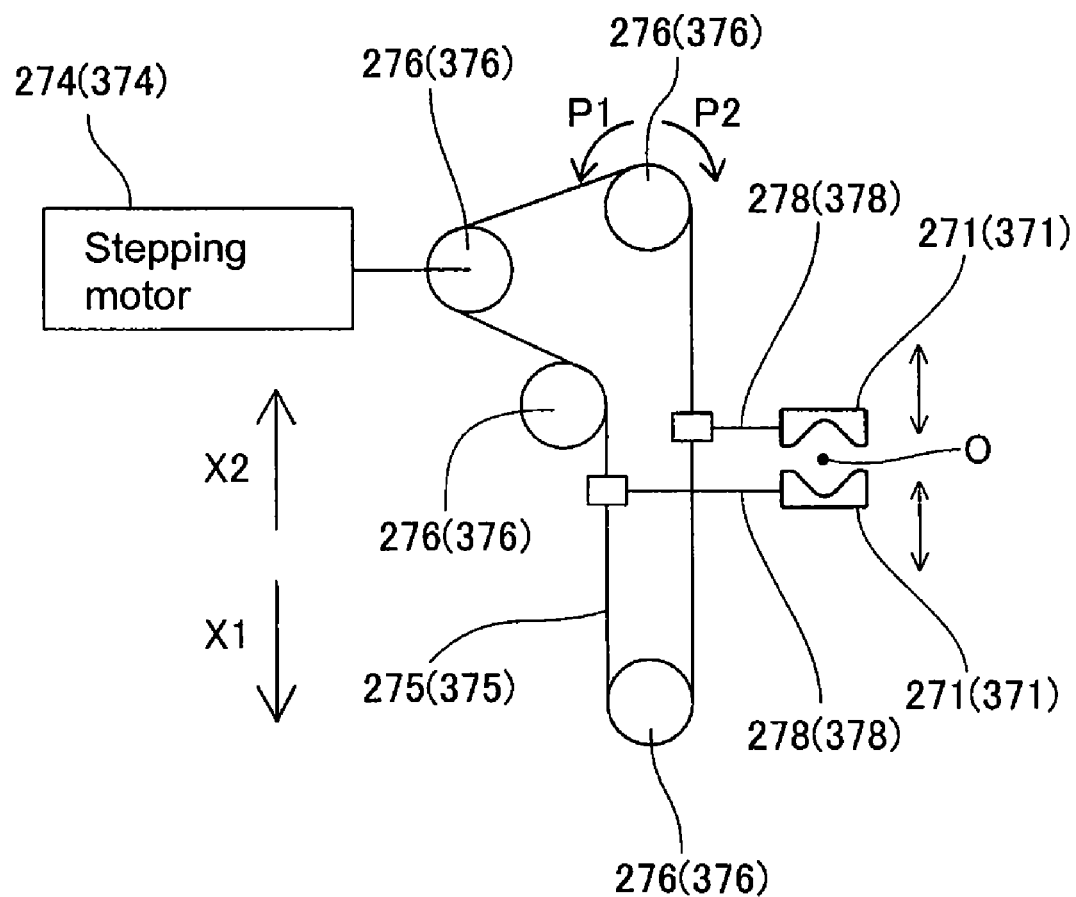
FIG. 14 is view describing the configuration of the fixing holder of the blood analyzer according to one embodiment shown in FIG. 1.

The coupling part 278 (378) attached to one of the pair of sandwiching parts 271 (371) is fixed at the upper portion of the two upper and lower stages extending horizontally in the directions of the arrows X1 and X2. The coupling part 278 (378) attached to the other of the pair of sandwiching parts 271 (371) is fixed to the lower portion of the two upper and lower stages extending horizontally in the directions of the arrows X1 and X2. Therefore, as shown in FIGS. 13 and 14, the pair of sandwiching parts 271 (371) are moved in the direction that the distance with respect to each other becomes small when the timing belt 275 (375) is turned in the direction of arrow P1, and moved in the direction that the distance with respect to each other becomes large when the timing belt 275 (375) is turned in the direction of arrow P2. Furthermore, the pair of sandwiching parts 271 (371) can be moved while maintaining the center position O of the region sandwiched by the pair of sandwiching parts 271 (371) at substantially the same position by being configured as above. Thus, the pair of sandwiching parts 271 (371) are attached to the timing belt 275 (375) by way of the coupling part 278 (378) such that the center position O of the region sandwiched by the pair of sandwiching parts 271 (371) is substantially the same position as the lowered position of the pipette 211 (311) lowered in the vertical direction when seen in plan view. The pair of sandwiching parts 271 (371) are also configured to move so as to contact from both sides while maintaining substantially the same distance with respect to the long vial 101 transferred to the aspiration position 600 (700). Therefore, when seen in plan view, the center axis of the long vial 101 fixedly held by the pair of sandwiching parts 271 (371) can be substantially coincided with the lowered position of the pipette 211 (311).

The position sensor 277 (377) has a cutout and is formed to a substantially U-shape. The position sensor 277 (377) is configured to detect the coupling part 278 (378) traversing the cutout. The CPU 51a of the control device 5, to be hereinafter described, can judge the position of the pair of sandwiching parts 271 (371) based on the detection result of the position sensor 277 (377), and the number of stepping of the stepping motor 274 (374).

The specimen setting portion open/close button 28 (38) is configured to be pushed by the user when performing the measurement of the priority specimen measured in preference to the continuous measurement specimen (specimen to be measured continuously) accommodated in the long vial 101 held at the rack 110.

The priority specimen measurement start button 29 (39) is configured to be pushed by the user. When the user pushes the priority specimen measurement start button 29 (39) after setting the long vial 101a or the microtube 102 accommodating the priority specimen in the first specimen setting portion 255a (355a) or the second setting portion 255b (355b), the set long vial 101 or the microtube 102 is taken into the measurement unit, and the measurement is started.

Figure 15:
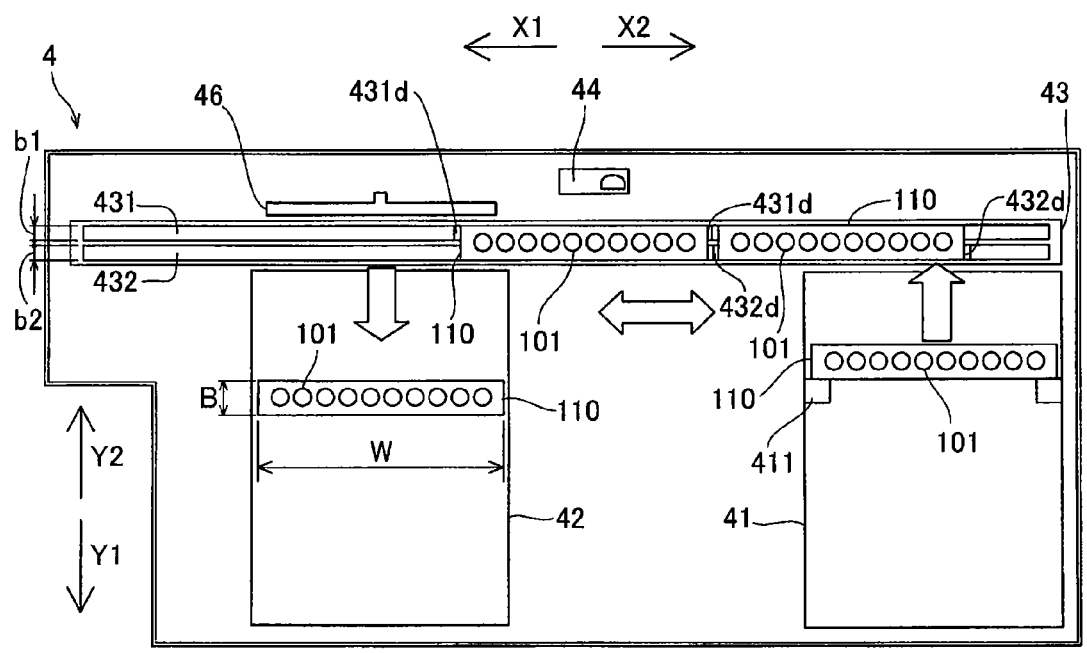
FIG. 15 is a plan view describing a specimen conveying device of the blood analyzer according to one embodiment shown in FIG. 1.

As shown in FIGS. 4 and 15, the specimen conveying device 4 includes a pre-analysis rack holder 41 capable of holding a plurality of racks 110 accommodating the long vial 101 for accommodating the specimen before being subjected to analysis, a post-analysis rack holder 42 capable of holding the plurality of racks 1110 accommodating the long vial 101 for accommodating the specimen after being subjected to analysis, a rack conveying unit 43 for linearly moving the rack 110 horizontally in the directions of the arrows X1 and X2, a barcode reader 44, a presence detection sensor 45 (see FIG. 4) for detecting the presence of the long vial 101, and a rack feed-out unit 46 for moving the rack 110 into the post-analysis rack holder 42.

The pre-analysis rack holder 41 includes a rack feed-in unit 411, where the rack 110 held by the pre-analysis rack holder 41 is pushed out onto the rack conveying unit 43 one at a time when the rack feed-in unit 411 moves in the direction of arrow Y2. The rack feed-in unit 411 is configured to be driven by a stepping motor (not shown) arranged at the lower side of the pre-analysis rack holder 41. The pre-analysis rack holder 41 has a regulating part 412 (see FIG. 4) in the vicinity of the rack conveying unit 43, and is configured to regulate the movement of the rack 110 so that the rack 110 that has once been pushed out onto the rack conveying unit 43 does not return to the pre-analysis rack holder 41.

The post-analysis rack holder 42 has a regulating part 421 (see FIG. 4) in the vicinity of the rack conveying unit 43, and is configured to regulate the movement of the rack 110 so that the rack 110 that has once been moved into the post-analysis rack holder 42 does not return to the rack conveying unit 43 side.

As shown in FIG. 3, the rack conveying unit 43 is configured to be able to convey the rack 110 such that the specimen is conveyed to the first provision position 43a for providing the specimen to the first measurement unit 2 and the second provision position 43b for providing the specimen to the second measurement unit 3. Furthermore, the rack conveying unit 43 is configured to be able to convey the rack 110 such that the specimen is conveyed to a specimen presence check position 43c for the presence detection sensor 45 to check the presence of the sample container 100 for accommodating the specimen and a read position 43d for the barcode reader 44 to read the barcode 101b (see FIG. 5) of the long vial 101 accommodating the specimen.

Figure 16:
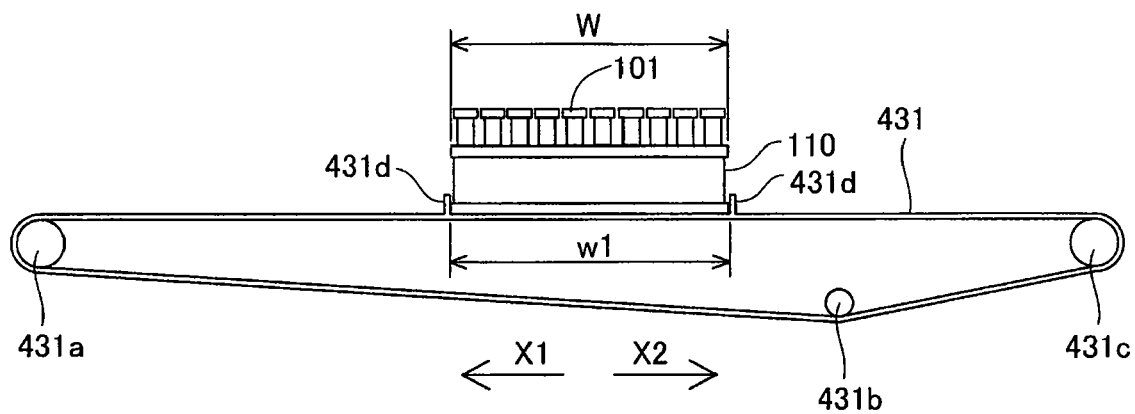
FIG. 16 is a side view describing the specimen conveying device of the blood analyzer according to one embodiment shown in FIG. 1.
Figure 17:
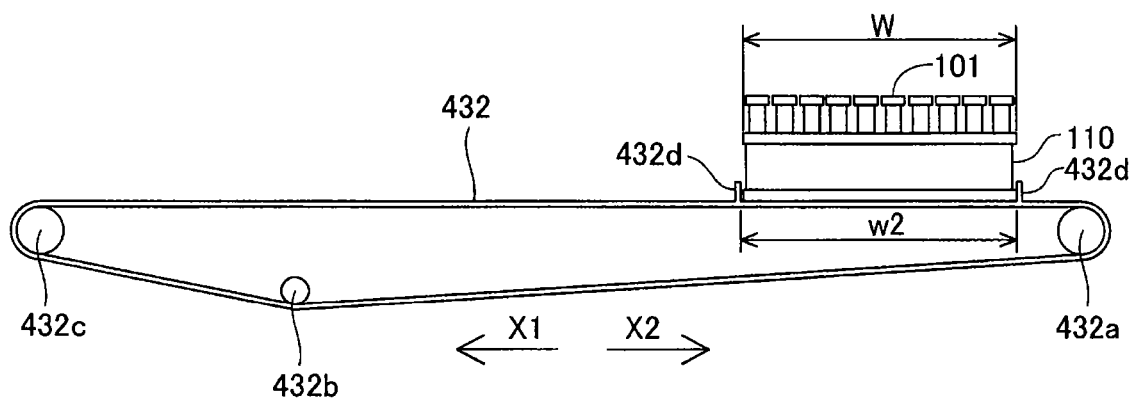
FIG. 17 is a side view describing the specimen conveying device of the blood analyzer according to one embodiment shown in FIG. 1.

As shown in FIGS. 4 and 15, the rack conveying unit 43 includes two belts, first belt 431 and second belt 432, which can move independent from each other. The widths b1 and b2 (see FIG. 15) in the directions of the arrows Y1 and Y2 of the first belt 431 and the second belt 432 have a magnitude of smaller than or equal to half of the width B of the directions of the arrows Y1 and Y2 of the rack 110, respectively. Thus, when the rack conveying unit 43 conveys the rack 110, the first belt 431 and the second belt 432 are both arranged in parallel so as not to exceed the width B of the rack 110. As shown in FIGS. 16 and 17, the first belt 431 and the second belt 432 are formed to an annular shape, and are arranged so as to surround the rollers 431a, 431b, 431c, and the rollers 432a, 432b, 432c, respectively. Projecting pieces 431d, 432d is formed by twos at the outer peripheral part of the first belt 431 and the second belt 432 so as to have an inner width w1 (see FIG. 16) and w2 (see FIG. 17) slightly (e.g., about 1 mm) larger than the width W in the directions of the arrows X1 and X2 of the rack 110. The first belt 431 is configured to move the rack 110 in the directions of the arrows X1 and X2 by being moved at the outer periphery of the rollers 431a to 431c by the stepping motor 431e (see FIG. 4) with the rack 110 held at the inner side of the projecting piece 431d. The second belt 432 is configured to move the rack 110 in the directions of the arrows X1 and X2 by being moved at the outer periphery of the rollers 432a to 432c by the stepping motor 432e (see FIG. 4) with the rack 110 held at the inner side of the projecting piece 432d. The first belt 431 and the second belt 432 are each configured to be able to move the rack 110 independent from each other.

The barcode reader 44 is configured to read the barcode 101b attached to each long vial 101 shown in FIG. 5, and to read the barcode 110a attached to the rack 110. The barcode reader 44 is also configured to read the barcode 101 while rotating the target long vial 101 in the horizontal direction by a rotating device (not shown) while being accommodated in the rack 110. Thus, even if the barcode 101b of the long vial 101 is attached to the opposite side with respect to the barcode reader 44, the barcode 101b can be directed to the barcode reader 44 side by rotating the long vial 101. The barcode 110a of the rack 110 is uniquely attached to each rack, and is used to manage the analysis result of the specimen, and the like.

The presence detection sensor 45 is a contact type sensor, and includes a curtain-shaped contact piece 451 (see FIG. 4), a light emitting element (not shown) for emitting light, and a light receiving element (not shown). The presence detection sensor 45 is configured such that the contact piece 451 is bent by contacting a detecting object to be detected, and as a result, the light exited from the light emitting element is reflected by the contact piece 451 and entered to the light receiving element. Therefore, when the long vial 101 to be detected accommodated in the rack 110 passes the lower side of the presence detection sensor 45, the contact piece 451 is bent by the long vial 101, and the presence of the long vial 101 can be detected.

The rack feed-out unit 46 is arranged so as to face the post-analysis rack holder 42 with the rack conveying unit 43 in between, and is configured to move horizontally in the direction of arrow Y1. Thus, when the rack 110 is conveyed to between the post-analysis rack holder 42 and the rack feed-out unit 46, the rack 110 is pushed and moved into the post-analysis rack holder 42 by moving the rack feed-out unit 46 to the post-analysis rack holder 42 side.

Figure 18:
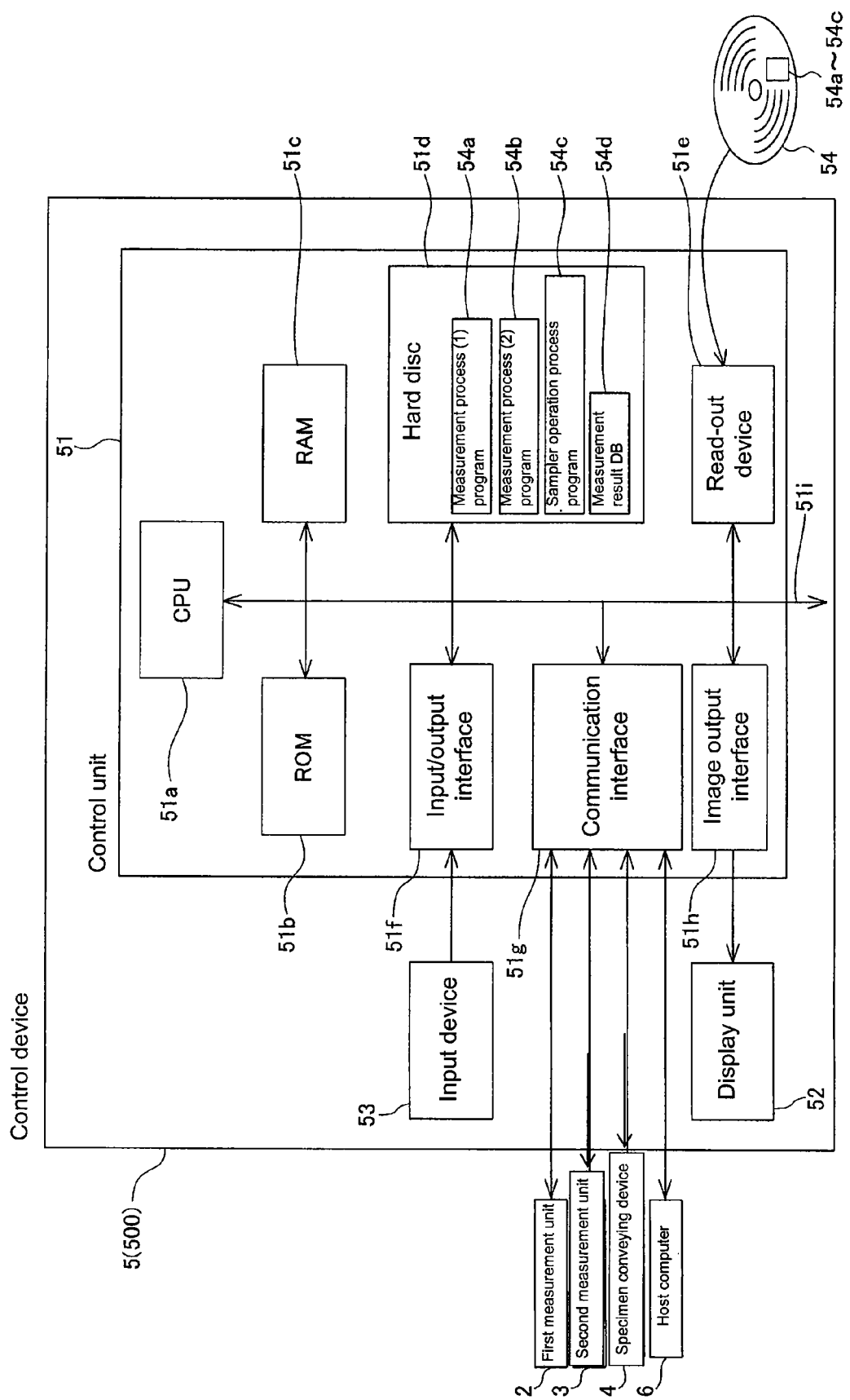
FIG. 18 is a block diagram describing a control device of the blood analyzer according to one embodiment shown in FIG. 1.
Figure 19:
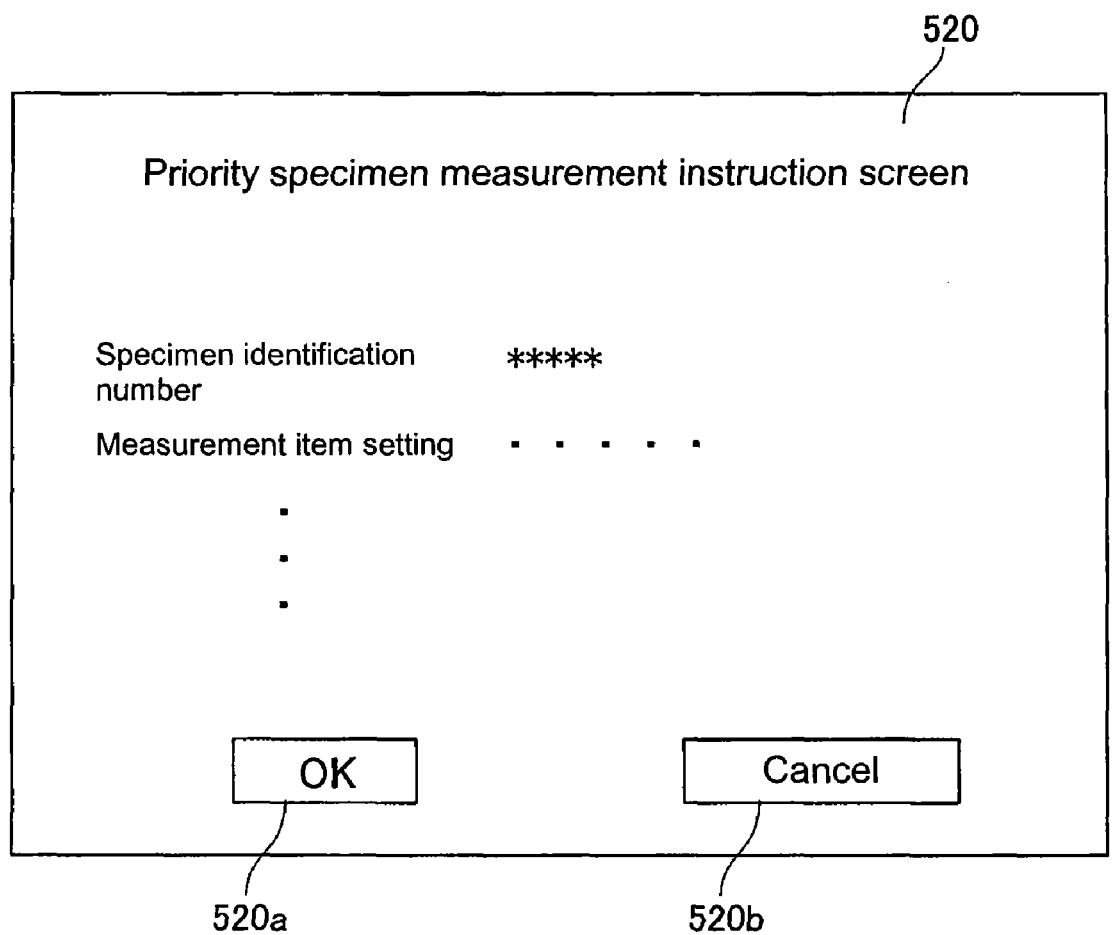
FIG. 19 is a view showing a priority specimen measurement instruction screen of the blood analyzer according to one embodiment shown in FIG. 1.

As shown in FIGS. 1 to 3 and 18, the control device 5 is configured by a personal computer (PC) and the like, and includes a control unit 51 (see FIG. 18) including CPU, ROM, and RAM, a display unit 52, and an input device 53. The display unit 52 is arranged to display the analysis result and the like obtained by analyzing the data of the digital signal transmitted from the first measurement unit 2 and the second measurement unit 3. As shown in FIG. 19, the display unit 52 is configured to display a priority specimen measurement instruction screen 520 for the user to perform input of a specimen identification number for identifying the specimen, measurement item setting, and the like in the measurement of the priority specimen that needs to be measured in preference to other specimens.

The configuration of the control device 5 will now be described. As shown in FIG. 18, the control device 5 is configured by a computer 500 mainly configured by a control unit 51, a display unit 52, and an input device 53. The control unit 51 is mainly configured by a CPU 51a, a ROM 51b, a RAM 51c, a hard disc 51d, a read-out device 51e, an input/output interface 51f, a communication interface 51g, and an image output interface 51h. The CPU 51a, the ROM 51b, the RAM 51c, the hard disc 51d, the read-out device 51e, the input/output interface 51f, the communication interface 51g, and the image output interface 51h are connected by a bus 51i.

The CPU 51a can execute computer programs stored in the ROM 51b and the computer programs loaded in the RAM 51c. The computer 500 serves as the control device 5 when the CPU 51a executes the application programs 54a, 54b and 54c.

The ROM 51b is configured by mask ROM, PROM, EPROM, EEPROM, and the like, and is recorded with computer programs to be executed by the CPU 51a, data used for the same, and the like.

The RAM 51c is configured by SRAM, DRAM, and the like. The RAM 51c is used to read out the computer programs recorded on the ROM 51b and the hard disc 51d. The RAM 51c is used as a work region of the CPU 51a when executing the computer programs.

The hard disc 51d is installed with various computer programs to be executed by the CPU 51a such as operating system and application program, as well as data used in executing the computer program. The measurement process (1) program 54a for the first measurement unit 2, the measurement process (2) program 54b for the second measurement unit 3, and the sample operation process program 54c for the specimen conveying device 4 are also installed in the hard disc 51d. When the CPU 51a executes such application programs 54a to 54c, the operation of each portion of the first measurement unit 2, the second measurement unit 3, and the specimen conveying device 4 is controlled. The measurement result database 54d is also installed in the hard disc 51d.

The read-out device 51e is configured by flexible disc drive, CD-ROM drive, DVD-ROM drive, and the like, and is able to read out computer programs and data recorded on a portable recording medium 54. The application programs 54a to 54c are stored in the portable recording medium 54, wherein the computer 500 reads out the application programs 54a to 54c from the portable recording medium 54, and installs the application programs 54a to 54c in the hard disc 51d.

The application programs 54a to 54c are not only provided by the portable recording medium 54, but are also provided through communication line (wired or wireless) from external devices communicably connected with the computer 500 through the communication line. For instance, the application programs 54a to 54c may be stored in the hard disc of the server computer on Internet, so that the computer 500 can access the server computer to download the application programs 54a to 54c and install the same in the hard disc 51d.

Operating system providing graphical user interface environment such as Windows (registered trademark) manufactured and sold by US Microsoft Co. is installed in the hard disc 51d. In the following description, the application programs 54a to 54c are assumed to operate on the operating system.

The input/output interface 51f is configured by serial interface such as USB, IEEE1394, RS-232C; parallel interface such as SCSI, IDE, IEEE1284; analog interface such as D/A converter, A/D converter, and the like. The input device 53 is connected to the input/output interface 51f, so that the user can input data to the computer 500 by using the input device 53.

The communication interface 51g is, for example, Ethernet (registered trademark) interface. The computer 500 transmits and receives data with the first measurement unit 2, the second measurement unit 3, the specimen conveying device 4, and the host computer 6 by using a predetermined communication protocol by means of the communication interface 51g.

The image output interface 51h is connected to the display unit 52 configured by LCD, CRT, or the like, and is configured to output an image signal corresponding to the image data provided from the CPU 51a to the display unit 52. The display unit 52 displays the image (screen) according to the input image signal.

According to the above configuration, the control unit 51 analyzes the component to be analyzed using the measurement results transmitted from the first measurement unit 2 and the second measurement unit 3, and acquires the analysis result (number of red blood cells, number of platelets, amount of hemoglobin, number of white blood cells, and the like).

As shown in FIG. 5, the rack 110 is formed with ten container accommodating portions 110b so as to accommodate ten sample containers 100 in a line. Each container accommodating portion 110b is provided with an opening 110c such that the barcode 101b of the accommodated long vial 101 can be visually recognized.

Figure 20:
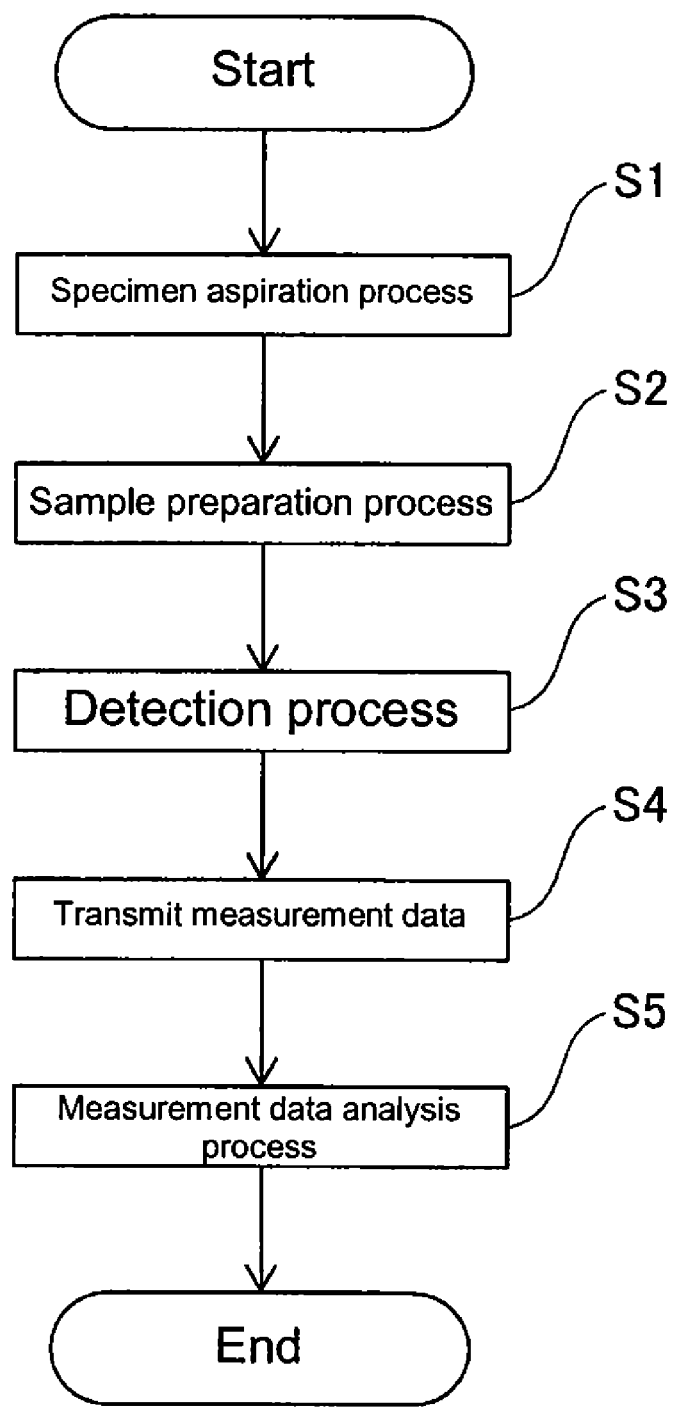
FIG. 20 is a flowchart describing a measurement processing operation by the measurement process program of the blood analyzer according to one embodiment shown in FIG. 1.

FIG. 20 is a flowchart describing the measurement processing operation by the measurement process program of the blood analyzer according to one embodiment shown in FIG. 1. The measurement processing operation by the measurement process programs 54a and 54b of the blood analyzer 1 according to one embodiment will be described with reference to FIGS. 3 and 20. The component to be analyzed is similarly measured in the first measurement unit 2 and the second measurement unit 3, and thus a case of measuring the component to be analyzed by the first measurement unit 2 will be described below as a representative example.

First, in step S1, the specimen is aspirated by the specimen aspiration section 21 from the sample container 100 conveyed to the aspiration position 600 shown in FIG. 3. In step S2, the detection sample is prepared by the sample preparation section 22 from the aspirated specimen, and in step S3, the component to be analyzed is detected by the detection section 23 from the detection sample. In step S4, the measurement data is transmitted from the first measurement unit 2 to the control device 5. Thereafter, in step S5, the component to be analyzed by the control unit 51 is analyzed based on the measurement result transmitted from the first measurement unit 2. The analysis of the specimen is completed and the operation is terminated by step S5.

Figure 21:
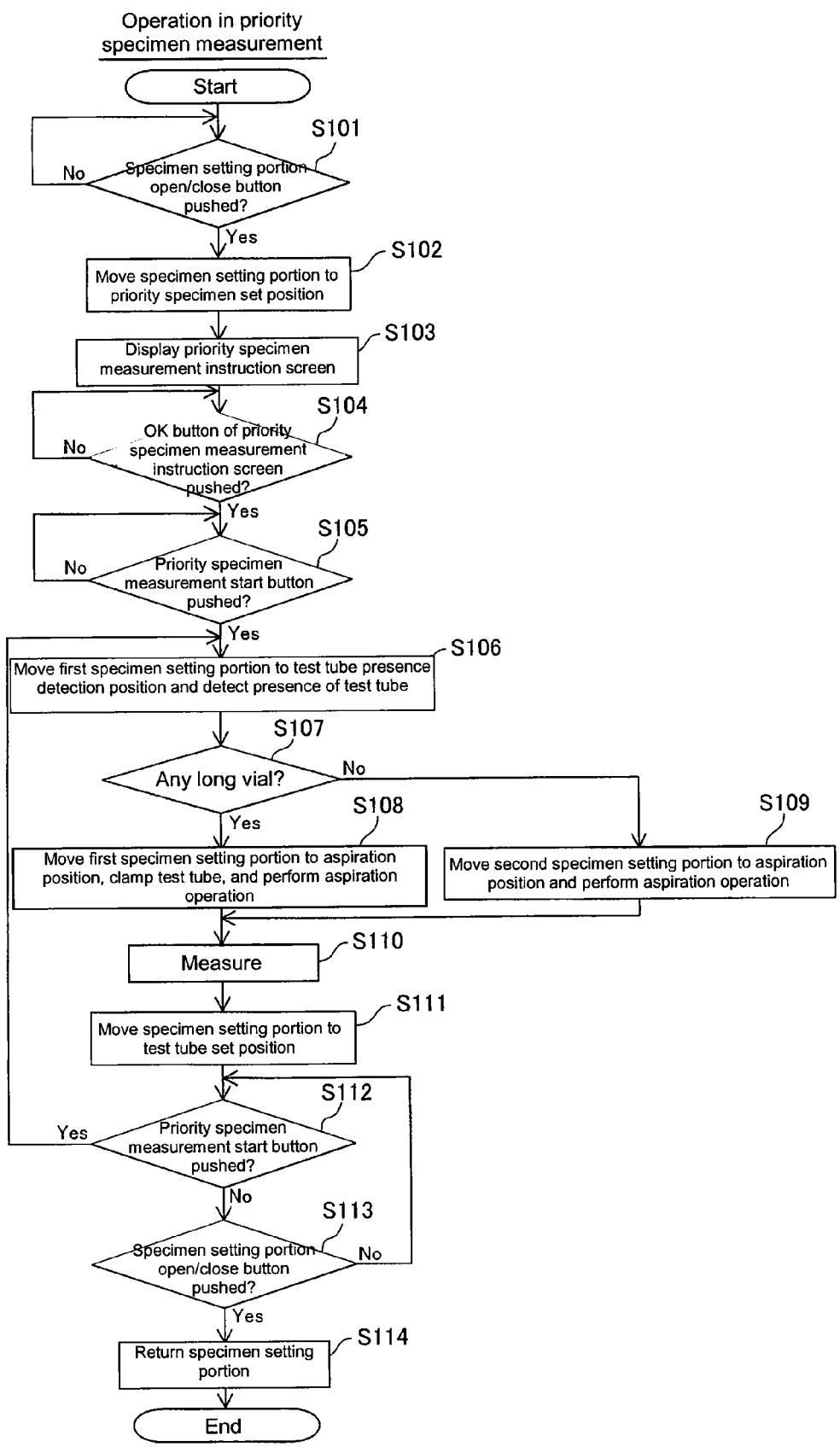
FIG. 21 is a flowchart describing the operation in the priority specimen measurement of the blood analyzer according to one embodiment shown in FIG. 1.

FIG. 21 is a flowchart describing the operation in the priority specimen measurement of the blood analyzer according to one embodiment shown in FIG. 1. FIGS. 22 to 25 are state diagrams for describing the operation in the priority specimen measurement of the blood analyzer according to one embodiment shown in FIG. 1. The operation in the priority specimen measurement of the blood analyzer 1 according to one embodiment will be described below with reference to FIGS. 1, 2, 19, and 21 to 25. In the present embodiment, the first measurement unit 2 and the second measurement unit 3 can measure the priority specimen independent from each other, and the operations in the priority specimen measurement in the first measurement unit 2 and the second measurement unit 3 are the same. Therefore, the operations in the priority specimen measurement in the first measurement unit 2 will be described herein as a representative example.

Figure 22:
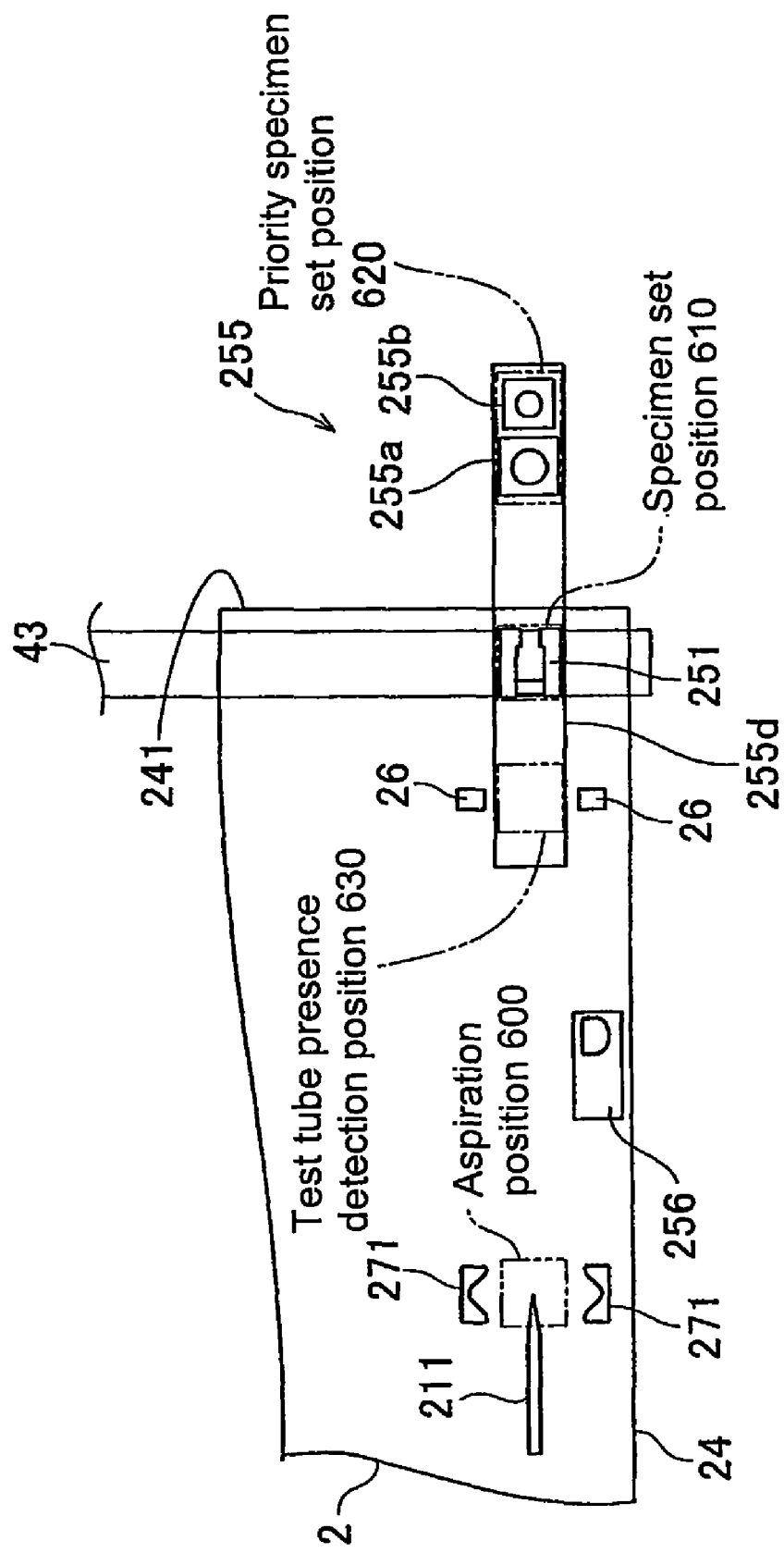
FIG. 22 is a state diagram describing the operation in the priority specimen measurement of the blood analyzer according to one embodiment shown in FIG. 1.

First, in step S101 shown in FIG. 21, the CPU 51a judges whether or not the specimen setting portion open/close button 28 (see FIGS. 1 and 2) is pushed, and repeats the judgment until the button is pushed. When the button is pushed, the movement portion 255d is moved so as to project out from the front surface portion 241 of the unit cover 24, and the first specimen setting portion 255a and the second specimen setting portion 255b are arranged at the priority specimen set position 620 in step S102, as shown in FIG. 22.

Figure 23:
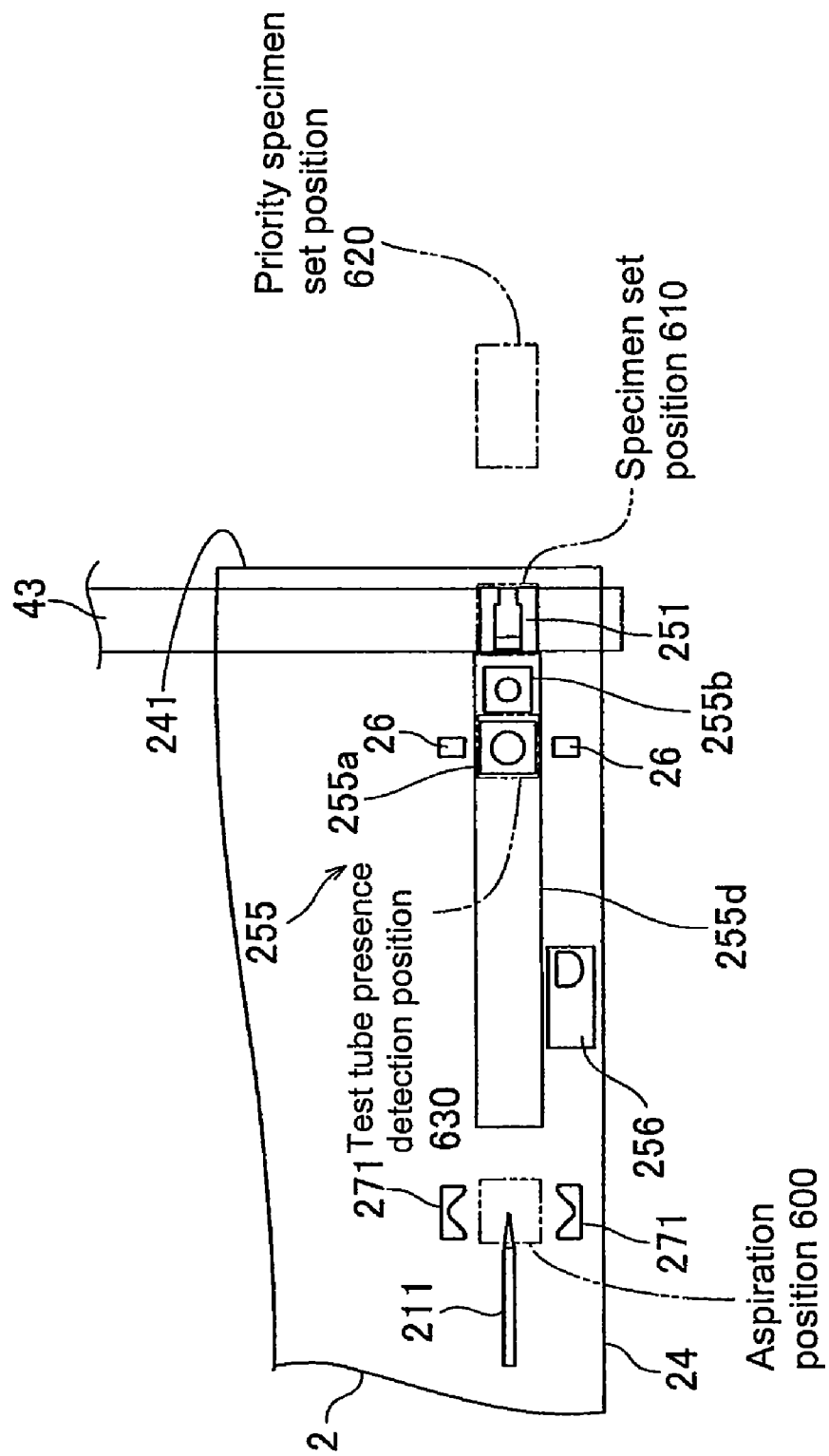
FIG. 23 is a state diagram describing the operation in the priority specimen measurement of the blood analyzer according to one embodiment shown in FIG. 1.

In step S103, the priority specimen measurement instruction screen 520 is displayed on the display unit 52, as shown in FIG. 19. In step S104, the user inputs the specimen identification number and sets the measurement items, and thereafter, the CPU 51a judges whether or not the OK button 520a displayed on the priority specimen measurement instruction screen 520 is pushed. This judgment is continued until the OK button 520a is pushed. When the cancel button 520b is pushed, the priority specimen measurement instruction screen 520 is terminated. When the OK button 520a of the priority specimen measurement instruction screen 520 is pushed, the CPU 51 judges whether or not the priority specimen measurement start button 29 (see FIGS. 1 and 2) is pushed in step S105. The user sets the long vial 101 or the microtube 102 accommodating the priority specimen in the first specimen setting portion 255a or the second specimen setting portion 522b after pushing the OK button 520a, and then pushes the priority specimen measurement start button 29. This judgment is repeated if the priority specimen measurement start button 29 is not pushed, and if the button is pushed, the first specimen setting portion 255a is moved to the test tube presence detection position 630, and the presence of the long vial 101 is detected by the presence detection section 26 in step S106, as shown in FIG. 23. The user sets the microtube 102 in the second specimen setting portion 255b with the lid of the microtube 102 detached when measuring the priority specimen accommodated in the microtube 102.

Figure 24:
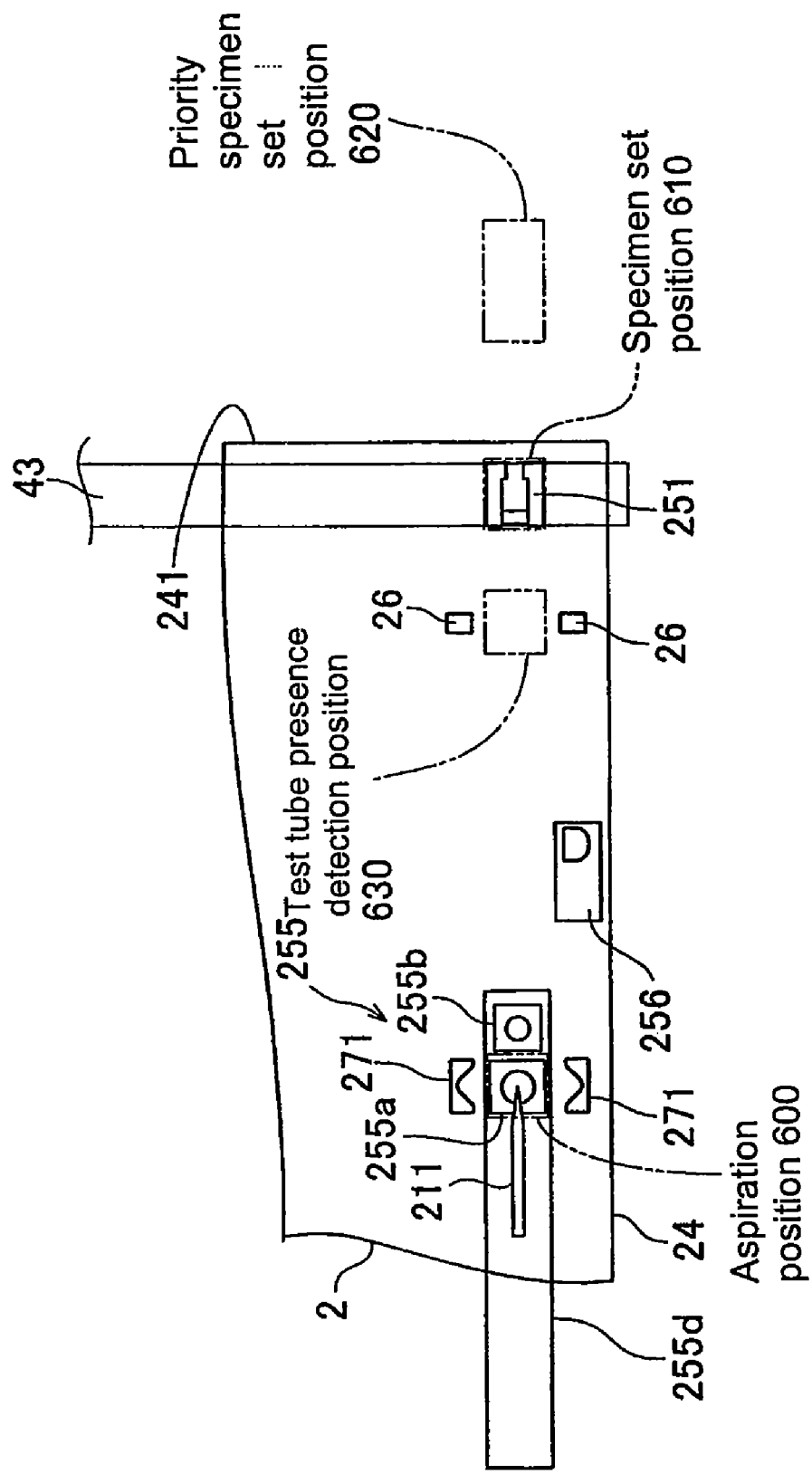
FIG. 24 is a state diagram describing the operation in the priority specimen measurement of the blood analyzer according to one embodiment shown in FIG. 1.

In step S107, the CPU 51a judges whether or not the long vial 101 is set in the first specimen setting portion 255a based on the detection result, where the first specimen setting portion 255a is moved to the aspiration position 600 if the long vial 101 is set in step S108, as shown in FIG. 24. Thereafter, the long vial 101 held by the first specimen setting portion 255a is sandwiched by the pair of sandwiching parts 271 of the fixing holder 27, and the long vial 101 is fixedly held such that the center axis of the long vial 101 is at the lowered position of the pipette 211. The pipette 211 is passed through the sealing lid 101a, and inserted to the inside of the long vial 101. Specifically, the pipette 211 is lowered by the stepping motor 218, which is rotatably driven at a predetermined rotary torque, passed through the sealing lid 101a, and thereafter, lowered until the distal end reaches the vicinity of the bottom portion of the long vial 101. After the blood in the long vial 101 is aspirated by the specimen aspiration section 21, the measurement of the priority specimen is performed in step S110.

Figure 25:
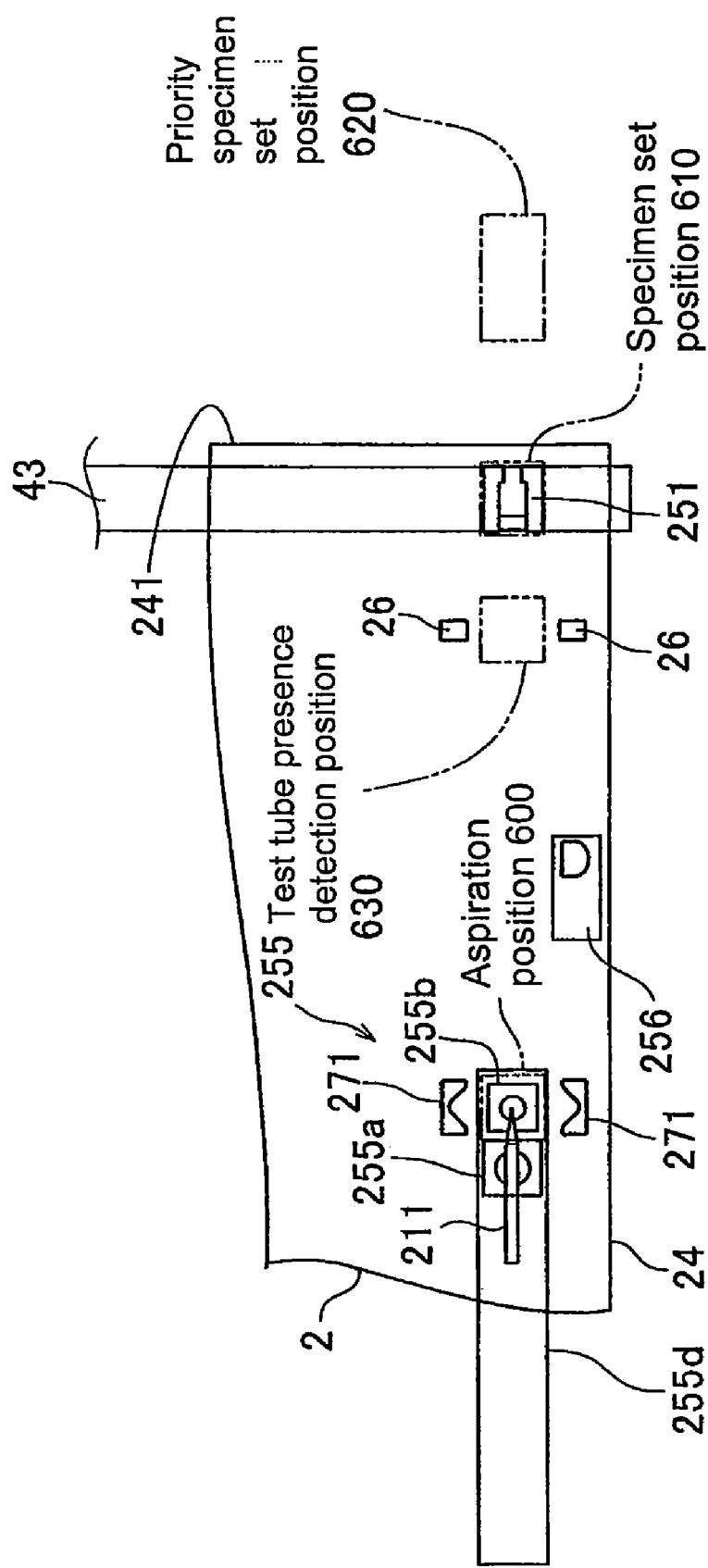
FIG. 25 is a state diagram describing the operation in the priority specimen measurement of the blood analyzer according to one embodiment shown in FIG. 1.

If the CPU 51a judges that the long vial 101 is not set in the first specimen setting portion 255a in step S107, the second specimen setting portion 255b is moved to the aspiration position 600 in step S109, as shown in FIG. 25. The pipette 211 is inserted to the inside of the microtube 102 held at the second specimen setting portion 255b, and lowered until the distal end reaches the bottom portion of the microtube 102. After the aspiration operation of the blood by the specimen aspiration section 21 is performed in this state, the process proceeds to step S110, and the measurement of the priority specimen is performed. The aspirating amount of blood in step S109 is less than the aspirating amount of blood in step S108.

After the aspiration of blood is completed, the first specimen setting portion 255a and the second specimen setting portion 255b are moved to the priority specimen set position 620 by the sample container transfer section 255 in step S111, as shown in FIG. 22. Thereafter, whether or not the priority specimen measurement start button 29 is pushed is judged in step S112. The user removes the long vial 101 or the microtube 102, where the blood has been aspirated, from the first specimen setting portion 255a or the second specimen setting portion 255b, then sets the long vial 101 or the microtube 102 accommodating a new priority specimen in the first specimen setting portion 255a or the second specimen setting portion 255b, and pushes the priority specimen measurement start button 29 to continuously perform the measurement of the priority specimen. When the user sets the long vial 101 or the microtube 102 accommodating the new priority specimen in the first specimen setting portion 255a or the second specimen setting portion 255b, and pushes the priority specimen measurement start button 29, the operation proceeds to step S106, and the measurement of the next priority specimen is continuously performed.

If the priority specimen measurement start button 29 is not pushed, the CPU 51a judges whether or not the specimen setting portion open/close button 28 is pushed in step S113. The user can terminate the measurement of the priority specimen by pushing the specimen setting portion open/close button 28. If the specimen setting portion open/close button 28 is not pushed, the judgments are repeated until either the priority specimen measurement start button 29 or the specimen setting portion open/close button 28 is pushed. If the specimen setting portion open/close button 28 is pushed, the movement portion 255d is moved in the direction of arrow Y2 to return the first specimen setting portion 255a and the second specimen setting portion 255b inside the unit cover 24 of the first measurement unit 2 in step S114, and the measurement operation of the priority specimen is terminated.

In the present embodiment, measurement of both the continuous measurement specimen that is continuously measured and the priority specimen that is measured in preference to the continuous measurement specimen can be responded by providing the rack 110 configured to be able to hold a plurality of long vials 101 accommodating the continuous measurement specimen that is continuously measured, and the first specimen setting portion 255a (355a) and the second specimen setting portion 255b (355b) configured to be able to hold the sample container 100 accommodating the priority specimen that is measured in preference to the continuous measurement specimen as described above. The sample container transfer section 255 (355) is provided to arrange the first specimen setting portion 255a (355a) and the second specimen setting portion 255b (355b) at the priority specimen set position 620 (720) by moving the movement portion 255d (355d) so as to pass the upper side of the long vial 101 held at the rack 110 at the position H1 higher than the upper end position H2 of the long vial 101 held in the rack 110, whereby a space occupied by the rack 110 and a space required when the first specimen setting portion 255a (355a) and the second specimen setting portion 255b (355b) are moved to the priority specimen set position 620 (720) are arranged to overlap each other in place view while suppressing the first specimen setting portion 255a (355a) and the second specimen setting portion 255b (355b) from interfering the rack 110 in time of the movement of the movement portion 255d (355d). Thus, the planar required space can be reduced compared to the case where the two spaces are arranged so as not to overlap each other in plan view. As a result, the installation area of the blood analyzer 1 can be reduced while responding to the measurements of both the continuous measurement specimen that is continuously measured and the priority specimen that is measured in preference to the continuous measurement specimen.

Furthermore, in the present embodiment, the hand portion 251 (351) is configured to transfer the long vial 101 accommodating the continuous measurement specimen from the rack 110 to the first specimen setting portion 255a (355a) by moving the long vial 101 accommodating the continuous measurement specimen in the up and down directions (direction of arrows Z1 and Z2) at substantially the same position in plan view, whereby the long vial 101 accommodating the continuous measurement specimen can be transferred from the rack 110 to the first specimen setting portion 255a (355a) in a minimum space in plan view, and thus the installation area of the blood analyzer 1 can be further reduced.

In the present embodiment, the unit cover 24 (34) including the front surface portion 241 (341) is provided, and the CPU 51a is configured so as to control the sample container transfer section 255 (355) such that the priority specimen set position 620 (720) is positioned on the front side (direction of arrow Y1 side) than the front surface portion 241 (341), the specimen set position 610 (710) is positioned on the back side (direction of arrow Y2 side) than the front surface portion 241 (341), whereby the user can set the long vial 101 or the microtube 102 accommodating the priority specimen with the first specimen setting portion 255a (355a) and the second specimen setting portion 255b (355b) positioned on the front side than the front surface portion 241 (341), and thus can easily set the long vial 101 or the microtube 102 at the first specimen setting portion 255a (355a) or the second specimen setting portion 255b (355b). Furthermore, the user is prevented from touching the long vial 101 being transferred since the transfer of the long vial 101 by the hand portion 251 (351) is carried out on the back side of the front surface portion 241 (341) on the side opposite to the front side of the front surface portion 241 (341) on which the user is positioned.

The embodiment disclosed herein is merely illustrative in all aspects and should not be recognized as being restrictive. The scope of the invention is defined by the claims rather than the description of the embodiment as described above, and the meaning equivalent to the claims and all modifications within the scope are encompassed therein.

For instance, the blood analyzer is described as one example of an analyzer in the present embodiment, but the present invention is not limited thereto, and the present invention may be applied to other analyzers as long as the measurement of both the continuous measurement specimen and the priority specimen can be responded.

Furthermore, an analyzer including two measurement units of the first measurement unit and the second measurement unit is described as one example of an analyzer in the present embodiment, but the present invention is not limited thereto, and may be an analyzer including one measurement unit or an analyzer including three or more measurement units.

The CPU, which is one of the control device, for controlling the sample container transfer section and the hand portion of both the first measurement unit and the second measurement unit, is described in the present embodiment, but the present invention is not limited thereto, and a plurality of CPUs for controlling the sample container transfer section and the hand portion of the first measurement unit and the second measurement unit independently may be provided.

The movement portion configured to linearly move in the horizontal direction is described as one example of a holder moving mechanism in the present embodiment, but the present invention is not limited thereto, and may be a holder moving mechanism configured to move in a diagonal direction inclined with respect to the horizontal direction as long as it is movable so as to pass the upper side of the continuous measurement specimen holder.

The hand portion configured to move in the up and down directions (direction of arrows Z1 and Z2) at substantially the same position in plan view is described as one example of a container transferring mechanism in the present embodiment, but the present invention is not limited thereto, and may be a container transferring mechanism configured to move in a direction inclined with respect to the up and down directions as long as the specimen container can be transferred from the continuous measurement specimen holder to the priority specimen holder.

The specimen aspiration section configured to adjust the lowering amount (lowered position) of the pipette depending on the type of specimen container is described as one example of an aspiration section in the present embodiment, but the present invention is not limited thereto, and may be an aspiration section configured to adjust the aspirating amount of the specimen depending on the type of specimen container.

Furthermore, the priority specimen holder including two specimen setting portions of the first specimen setting portion and the second specimen setting portion is described as one example of a priority specimen holder in the present embodiment, but the present invention is not limited thereto, and may be a priority specimen holder including only one specimen setting portion or may be a priority specimen holder including three or more specimen setting portions.

An analyzer including separate unit covers for each measurement unit is described as one example of an analyzer in the present embodiment, but the present invention is not limited thereto, and may be an analyzer without an unit cover or may be an analyzer including one unit cover for accommodating a plurality of measurement units.

The movement portion moved so as to intersect the conveyance path of the specimen container by the conveying mechanism in plan view is described as one example of a holder moving mechanism in the present embodiment, but the present invention is not limited thereto, and may be a holder moving mechanism moved in parallel to the conveyance path of the specimen container by the conveying mechanism.

The invention claimed is:

1. An analyzer comprising:
a first specimen holder configured to hold a plurality of first specimen containers accommodating a continuous measurement specimen to be continuously measured;
a conveying assembly for conveying the first specimen containers held in the first specimen holder;
a second specimen holder arranged at a position higher than an upper end of the first specimen containers held in the first specimen holder and configured to hold at least one of the first specimen containers and a second specimen container accommodating a priority measurement specimen to be measured in preference to the continuous measurement specimen;

a holder moving assembly for moving the second specimen holder so as to pass the upper side of at least one of the first specimen containers held in the first specimen holder;

a container transferring assembly for transferring at least one of the first specimen containers from the first specimen holder to the second specimen holder; and a controller for controlling the holder moving assembly and the container transferring assembly to execute steps of:

raising at least one of the first specimen containers held in the first specimen holder to the upper side of the second specimen holder when the second specimen holder is not vertically aligned with the at least one of the first specimen containers, moving the second specimen holder to the lower side of the raised first specimen container, and setting the first specimen container in the second specimen holder by lowering the first specimen container.

2. The analyzer according to claim 1, wherein the second specimen holder includes a first holder for holding the first and the second specimen containers, and a second holder for holding the second specimen container when the second specimen container is a microtube, the second holder being arranged in front of the first holder.

3. The analyzer according to claim 1, further comprising a front surface cover arranged on the front surface side of the analyzer; wherein the controller controls the holder moving assembly so that the position where the first specimen container is set in the second specimen holder is behind the front surface cover.

4. The analyzer according to claim 3, wherein the second specimen holder includes a holder for holding the second specimen container; and the controller controls the holder moving assembly and the container transferring assembly to execute further steps of:

accepting an instruction to move the second specimen holder, and moving the second specimen holder so that the holder is arranged in front of the front surface cover.

5. The analyzer according to claim 1, wherein the holder moving assembly is configured to move the second specimen holder in a substantially horizontal direction at the upper side of the first specimen containers held in the first specimen holder.

6. The analyzer according to claim 1, wherein the holder moving assembly is configured to move the second specimen holder so as to be substantially orthogonal to a conveyance path of the first specimen containers by the conveying assembly in plan view.

7. The analyzer according to claim 1, wherein the controller controls the conveying assembly to execute further a step of:

conveying the first specimen containers held in the first specimen holder with the second specimen holder arranged at a position for receiving the second specimen container.

8. The analyzer according to claim 1, further comprising a detection section commonly used in the measurement of both the continuous measurement specimen and the priority measurement specimen.

9. The analyzer according to claim 8, wherein the continuous measurement specimen and the priority measurement specimen are blood; and the detection section is configured to detect blood cells in the blood.

10. The analyzer according to claim 1, further comprising an aspiration section for aspirating the specimen from the first and the second specimen containers set in the second specimen holder; wherein the holder moving assembly is configured to move the second specimen holder to a position where the specimen is aspirated by the aspiration section.

11. The analyzer according to claim 1, wherein the second specimen holder, the holder moving assembly, and the container transferring assembly are arranged in plurals; and the analyzer further includes, a plurality of measurement units each including the second specimen holder, the holder moving assembly, and the container transferring assembly, a conveying device, including the first specimen holder and the conveying assembly, for conveying the first specimen container to the plurality of measurement units, and a control unit, including the controller, for controlling the plurality of measurement units and the conveying device.

12. An analyzer comprising:

a first specimen holder configured to hold a plurality of first specimen containers accommodating a continuous measurement specimen to be continuously measured;

a conveying assembly for conveying the first specimen containers held in the first specimen holder;

a second specimen holder arranged at a position higher than an upper end of the first specimen containers held in the first specimen holder and configured to hold a second specimen container accommodating a priority measurement specimen to be measured in preference to the continuous measurement specimen; and a holder moving assembly for moving the second specimen holder between a first position higher than the upper end of the first specimen containers held in the first specimen holder where the second specimen container is manually set in the second specimen holder and a second position higher than the upper end of the first specimen containers held in the first specimen holder where the priority measurement specimen is aspirated from the second specimen container so as to pass the upper side of at least one of the first specimen containers held in the first specimen holder.

13. The analyzer according to claim 12, wherein the second specimen holder is configured to hold at least one of the first specimen containers; and the analyzer further includes, a container transferring assembly for transferring at least one of the first specimen containers from the first specimen holder to the second specimen holder.

14. The analyzer according to claim 13, wherein the container transferring assembly is configured to transfer the first specimen container from the first specimen holder to the second specimen holder by moving the first specimen container in an up and down direction at substantially the same position in plan view.

15. The analyzer according to claim 12, wherein
the second specimen holder and the holder moving assembly are arranged in plurals; and
the analyzer further includes,
  a plurality of measurement units each including the second specimen holder and the holder moving assembly, and
  a conveying device, including the first specimen holder and the conveying assembly, for conveying the first specimen container to the plurality of measurement units.

16. An analyzer comprising:
a first specimen holder configured to hold a plurality of first specimen containers accommodating a continuous measurement specimen to be continuously measured;
a second specimen holder arranged at a position higher than an upper end of the first specimen containers held in the first specimen holder and configured to hold at least one of the first specimen containers and a second specimen container accommodating a priority measurement specimen to be measured in preference to the continuous measurement specimen;
a holder moving assembly for moving the second specimen holder so as to pass the upper side of at least one of the first specimen containers held in the first specimen holder;
a container transferring assembly for transferring at least one of the first specimen containers from the first specimen holder to the second specimen holder; and
an aspiration section for aspirating the specimen from the first and the second specimen containers set in the second specimen holder; wherein
the holder moving assembly is configured to move the second specimen holder from a first position where the second specimen container is manually set in the second specimen holder to a second position where the specimen is aspirated by the aspiration section, and the first and second positions are higher than the upper end of the first specimen containers held in the first specimen holder.

17. The analyzer according to claim 16, further comprising a conveying assembly for conveying the first specimen containers held in the first specimen holder.

18. An analyzer comprising:
a first specimen holder configured to hold a plurality of first specimen containers accommodating a continuous measurement specimen to be continuously measured;
a second specimen holder arranged at a position higher than an upper end of the first specimen containers held in the first specimen holder and configured to hold at least one of the first specimen containers and a second specimen container accommodating a priority measurement specimen to be measured in preference to the continuous measurement specimen;
a holder moving assembly for moving the second specimen holder so as to pass the upper side of at least one of the first specimen containers held in the first specimen holder;
a container transferring assembly for transferring at least one of the first specimen containers from the first specimen holder to the second specimen holder; and
an aspiration section for aspirating the specimen from the first and the second specimen containers set in the second specimen holder; wherein
the holder moving assembly is configured to move the second specimen holder to a position where the specimen is aspirated by the aspiration section,
the second specimen holder includes a first holder for holding the first and the second specimen containers, and a second holder for holding the second specimen container when the second specimen container is a microtube, and
the holder moving assembly is configured to move the second specimen holder between a first position where the first specimen container is set in the first holder by the container transferring assembly and a second position where the specimen is aspirated from the first specimen container held in the first holder by the aspiration section, and is configured to move the second specimen holder between a third position where the second specimen container is manually set in the second holder and a fourth position where the specimen is aspirated from the second specimen container held in the second holder by the aspiration section.

19. The analyzer according to claim 16, wherein
the second specimen holder, the holder moving assembly, the container transferring assembly, and the aspiration section are arranged in plurals; and
the analyzer further includes,
a plurality of measurement units each including the second specimen holder, the holder moving assembly, the container transferring assembly, and the aspiration section, and
a conveying device, including the first specimen holder, for conveying the first specimen container to the plurality of measurement units.

* * * * *